United States Patent
Gangwar et al.

(10) Patent No.: US 11,751,946 B2
(45) Date of Patent: *Sep. 12, 2023

(54) SYSTEM FOR POSE ESTIMATION OF THREE-DIMENSIONAL BONE MODELS IN SURGICAL PLANNING A JOINT REPLACEMENT PROCEDURE

(71) Applicant: STRYKER EUROPEAN OPERATIONS HOLDINGS LLC, Kalamazoo, MI (US)

(72) Inventors: Ashish Gangwar, Gurgaon (IN); Kanishk Sethi, Gurgaon (IN); Anup Kumar, Gurgaon (IN); Ryan Sellman, Mahwah, NJ (US); Peter Sterrantino, Mahwah, NJ (US); Manoj Kumar Singh, Mahwah, NJ (US)

(73) Assignee: STRYKER EUROPEAN OPERATIONS HOLDINGS LLC, Kalamazoo, MI (US)

(*) Notice: Subject to any disclaimer, the term of this patent is extended or adjusted under 35 U.S.C. 154(b) by 37 days.

This patent is subject to a terminal disclaimer.

(21) Appl. No.: 17/473,265

(22) Filed: Sep. 13, 2021

(65) Prior Publication Data

US 2021/0401506 A1 Dec. 30, 2021

Related U.S. Application Data

(63) Continuation of application No. 16/856,685, filed on Apr. 23, 2020, now Pat. No. 11,147,627, which is a (Continued)

(51) Int. Cl.
*G06T 15/00* (2011.01)
*A61B 34/10* (2016.01)
(Continued)

(52) U.S. Cl.
CPC ............... *A61B 34/10* (2016.02); *G06T 7/73* (2017.01); *G06T 19/20* (2013.01);
(Continued)

(58) Field of Classification Search
CPC ........ A61B 2090/364; A61B 2090/376; A61B 34/10; A61B 2034/105; A61B 2090/374;
(Continued)

(56) References Cited

U.S. PATENT DOCUMENTS 10,646,137 B2* 5/2020 Lintz .................... A61B 5/1079
10,667,867 B2* 6/2020 Gangwar ................. G06T 7/73
(Continued)

*Primary Examiner* — Phu K Nguyen
(74) *Attorney, Agent, or Firm* — Polsinelli PC

(57) ABSTRACT

A system for processing patient data associated with a joint of a patient. The system comprising a computing device executing instructions to generate a 3D patient bone model of the joint in a non-weighted pose. The instructions rearrange 3D first and second bone models in order to mimic a weighted pose of the joint of the patient from a 2D image of the joint of the patient in a weighted pose by performing the steps of: generating a plurality of 2D projections of poses of the 3D patient bone model; comparing the plurality of 2D projections to contour lines of the first bone and the second bone in the 2D image; identifying particular 2D projections that best-fit a shape and size of the contour lines; and arranging the 3D first and second bone models relative to each other according to orientations represented by the particular 2D projections that were identified.

26 Claims, 14 Drawing Sheets
(3 of 14 Drawing Sheet(s) Filed in Color)

Related U.S. Application Data continuation of application No. 15/969,861, filed on May 3, 2018, now Pat. No. 10,667,867.

(60) Provisional application No. 62/500,823, filed on May 3, 2017.

(51) Int. Cl.
  G06T 7/73 (2017.01)
  G06T 19/20 (2011.01)
  *A61B 90/00* (2016.01)
  *G06T 11/00* (2006.01)

(52) U.S. Cl.
  CPC ... *A61B 2034/105* (2016.02); *A61B 2090/364* (2016.02); *A61B 2090/374* (2016.02); *A61B 2090/376* (2016.02); *G06T 11/006* (2013.01); *G06T 2200/08* (2013.01); *G06T 2207/10081* (2013.01); *G06T 2207/10088* (2013.01); *G06T 2207/10116* (2013.01); *G06T 2207/30008* (2013.01); *G06T 2219/2004* (2013.01)

(58) Field of Classification Search
  CPC . G06T 2207/10116; G06T 2207/10088; G06T 2207/10081; G06T 2200/08; G06T 2219/2004; G06T 11/006; G06T 7/73; G06T 2007/30008; G06T 19/20
  USPC .......................................................... 345/418
  See application file for complete search history.

(56) References Cited

U.S. PATENT DOCUMENTS

| | | | | |
|---|---|---|---|---|
| 10,716,631 | B2* | 7/2020 | Tolkowsky | A61B 6/505 |
| 10,849,693 | B2* | 12/2020 | Lang | A61F 2/389 |
| 11,147,627 | B2* | 10/2021 | Gangwar | G06T 19/20 |
| 2020/0405399 | A1* | 12/2020 | Steinberg | G06N 20/00 |

* cited by examiner

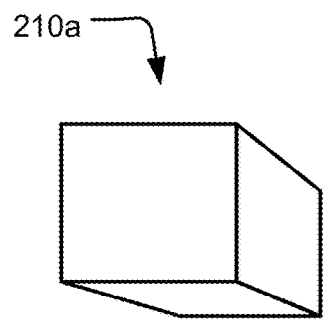
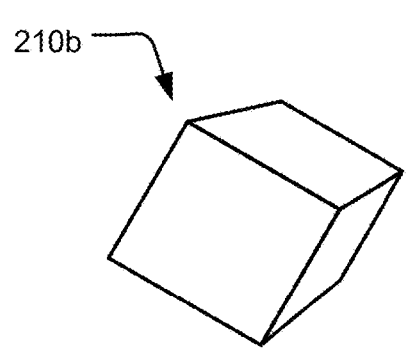
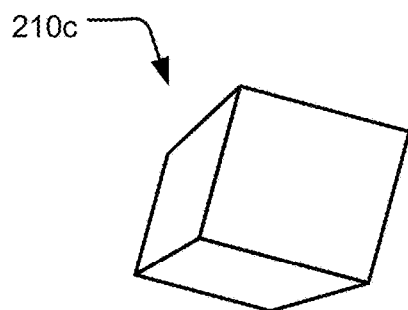
FIG. 13A        FIG. 13B        FIG. 13C
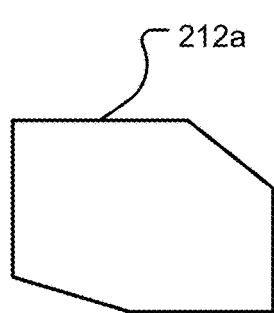
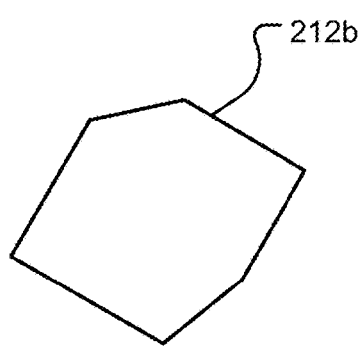
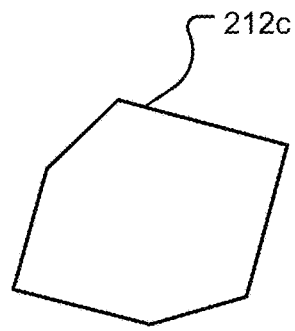
FIG. 14A        FIG. 14B        FIG. 14C

SYSTEM FOR POSE ESTIMATION OF THREE-DIMENSIONAL BONE MODELS IN SURGICAL PLANNING A JOINT REPLACEMENT PROCEDURE

CROSS-REFERENCE TO RELATED APPLICATIONS

The present application is a continuation of application Ser. No. 16/856,685 filed Apr. 23, 2020, which application is a continuation of application Ser. No. 15/969,861 filed May 3, 2018, now U.S. Pat. No. 10,667,867, which application claims priority under 35 U.S.C. § 119 to U.S. Provisional Patent Application No. 62/500,823, which was filed May 3, 2017. All of the applications mentioned above are hereby incorporated by reference in their entirety into the present application.

TECHNICAL FIELD

Aspects of the present disclosure involve methods of lateral and anterior-posterior pose estimation of bone models in surgical planning a total ankle replacement, and, more particularly, involve methods of mapping weight bearing conditions of a foot from standing X-ray images to bone models generated from medical images of a supine patient.

BACKGROUND

Total ankle replacement ("TAR") procedures involve replacement of the ankle joint with an artificial implant that is designed to treat a particular condition, such as arthritis or fracture of a bone forming the joint. A conventional TAR procedure may include scanning the damaged foot and leg of the patient with medical imaging machine (e.g., CT machine, MRI machine) while the patient is in a supine position. The individual bones in each of the scans or images of the foot and leg are then segmented. A three-dimensional ("3D") bone model of the bones is generated from the segmented images, and then the surgeon may plan the surgical procedure using the patient specific 3D bone models. Surgical planning may include determining implant size and position, resection depths and positions relative to the bones, and surgical approaches, among other parameters. Once planning is complete, the surgery is then performed according to the plan.

One particular error-factor in TAR procedures is valid ankle pose estimation during the surgical planning steps of the procedure given the image scans forming the basis of the 3D bone models are not performed under weight bearing conditions. More particularly, the image scans performed on a non-standing, supine patient depict the bones of the foot and leg (e.g., tibia, fibula, talus, calcaneus) in an un-weighted state or condition. That is, the weight of the patient body is not acting on the bones of the leg and foot during the imaging scans. Thus, the 3D models of the bones of the leg and foot are modeled as if the bones are un-weighted. In this way, any surgical planning that takes place based on 3D models does not take into account a standing or weighted position of the bones relative to each other or relative to the floor. This can result in less than desirable surgical outcomes.

Accordingly, there is a need in the art for system and methods that address these shortcomings, among others.

SUMMARY

Aspects of the present disclosure are directed to improving TAR procedures and planning for the same by providing methods of mapping weight bearing conditions of a foot from standing X-ray images to bone models generated from medical images (e.g., computed tomography ("CT") images, magnetic resonance images ("MRI"), among others) of a supine patient.

In certain instances, the method may include the following steps: (1) surface projection of 3D bone model to form 2D image of bone model: project the surface of the 3D bone model (generated from non-standing CT images) in lateral and anteroposterior views to form 2D images of bone model; (2) contour extraction of X-ray images: segment the object region in the X-ray images in lateral and anteroposterior views as defined by the bone boundary; (3) shape match (1) and (2): register or map the 2D images of the bone models with the segmented X-ray images in one or both of the lateral and anteroposterior views; (4) pose update: use the point correspondences from the shape matching step (3) to update pose of the 2D images of the bone model; (5) iterate: repeat steps (1) to (4) until convergence.

Aspects of the present disclosure may involve one or more tangible computer-readable storage media storing computer-executable instructions for performing a computer process on a computing system. In certain instances, the computer process may include: receiving first patient bone data of a patient leg and foot in a first pose, the first patient bone data generated via a first imaging modality, the first pose may include a position and orientation of the patient leg relative to the patient foot as defined in the first patient bone data. The computer process may further include receiving second patient bone data of the patient leg and foot in a second pose, the second patient bone data generated via a second imaging modality that may be different from the first imaging modality, the second pose may include a position and orientation of the patient leg relative to the patient foot as defined in the second patient bone data. The computer process may further include generating a three-dimensional (3D) bone model of the patient leg and foot from the first patient bone data, the 3D bone model may include a plurality of 3D bone models arranged in the first pose. And, the computer process may further include modifying the 3D bone model of the patient leg and foot such that the plurality of 3D bone models are reoriented into a third pose that matches a particular arrangement of bones in the patient leg and foot in the second pose.

In certain instances, the first imaging modality may be computed tomography.

In certain instances, the second imaging modality may be X-ray.

In certain instances, the first pose may include a non-standing position and orientation of the patient leg relative to the patient foot.

In certain instances, the second pose may include a standing position and orientation of the patient leg relative to the patient foot.

In certain instances, the modifying the 3D bone model may include causing first bone contour lines of the plurality of 3D bone models to align with second bone contour lines of the second patient bone data.

In certain instances, the one or more tangible computer-readable storage media may further include importing the 3D bone model and the second patient bone data into a common coordinate system.

In certain instances, the second patient bone data may include a lateral X-ray image of the patient leg and foot in the second pose, a medial X-ray image of the patient leg and foot in the second pose, and an anteroposterior X-ray image of the patient leg and foot in the second pose.

In certain instances, the modifying the 3D bone model may include aligning the plurality of 3D bone models with corresponding bones of the patient leg and foot in the second patient bone data, wherein the aligning may be done in lateral, medial, and anteroposterior views of the plurality of 3D bone models so as to match the orientation of the patient leg and foot in the lateral X-ray image and the anteroposterior X-ray image.

In certain instances, the modifying the 3D bone model of the patient leg and foot may be performed manually.

In certain instances, the modifying the 3D bone model of the patient leg and foot may be performed automatically.

In certain instances, the modifying the 3D bone model of the patient leg and foot may be performed automatically by positionally matching landmarks in the plurality of 3D bone models and the second patient bone data.

In certain instances, the first patient bone data and the second patient bone data are the results of two different imaging events.

In certain instances, the second imaging modality may be X-ray, and the second patient bone data may include X-ray images, the computer process further may include: segmenting bones of the patient leg and foot in the X-ray images; and generating bone contour lines along a perimeter of at least some of the bones in the X-ray images.

In certain instances, the one or more tangible computer-readable storage media may further include: generating a plurality of poses for each of the plurality of 3D bone models; generating a plurality of two-dimensional (2D) projections from the plurality of poses for each of the plurality of 3D bone models; and comparing the bone contour lines to the plurality of 2D projections, and identifying particular 2D projections from the plurality of 2D projections that most closely match the bone contour lines.

In certain instances, the one or more tangible computer-readable storage media may further include: arranging the plurality of 3D bone models according to particular orientations of the particular 2D projections associated with each of the bones.

In certain instances, the one or more tangible computer-readable storage media may further include: preoperatively planning a total ankle replacement procedure using the plurality of 3D bone models being reoriented into the third pose.

In certain instances, the one or more tangible computer-related storage media may further include: limiting a number of the plurality of poses that are generated to only such poses that are permissible given bio-kinematics of the bones making up the plurality of 3D bone models.

Aspects of the present disclosure may involve a system for processing patient data. In certain instances, the system may include: a network interface configured to receive one or more sets of patient data; a processing device in communication with the network interface; and a computer-readable medium in communication with the processing device configured to store information and instructions that, when executed by the processing device, performs the operations of: receiving first patient data may include at least one two-dimensional (2D) image of a patient leg and foot in a weighted pose; receiving second patient data may include computed tomography (CT) images of the patient leg and foot in a non-weighted pose, the first patient data and the second patient data being the result of separate imaging events; generating a three-dimensional (3D) bone model of the patient leg and foot from the CT images, the 3D bone model may include a plurality of 3D bone models representing individual bones of the patient leg and foot; and rearranging the plurality of 3D bone models to mimic the weighted pose of the patient leg and foot in the at least one 2D image.

In certain instances, the system may further include: generating a plurality of 2D projections of poses of the plurality of 3D bone models; comparing the plurality of 2D projections to contour lines outlining perimeters of bones of the patient leg and foot in the at least one 2D image; and identifying particular 2D projections from the plurality of 2D projections that best-fit a shape and size of the contour lines.

BRIEF DESCRIPTION OF THE DRAWINGS

The patent application file contains at least one drawing executed in color. Copies of this patent or patent application publication with color drawing(s) will be provided by the Office upon request and payment of necessary fee.

Example embodiments are illustrated in referenced figures of the drawings. It is intended that the embodiments and figures disclosed herein are to be considered illustrative rather than limiting.

FIGS. 13A, 13B, and 13C depict an object, representing an individual bone of a 3D bone model of a patient's foot, in three different poses, respectively.

FIG. 14A depicts a 2D projection of the outer boundary of the object in the pose as shown in FIG. 13A.

FIG. 14B depicts a 2D projection of the outer boundary of the object in the pose as shown in FIG. 13B.

FIG. 14C depicts a 2D projection of the outer boundary of the object in the pose as shown in FIG. 13C.

DETAILED DESCRIPTION

Figure 1A:
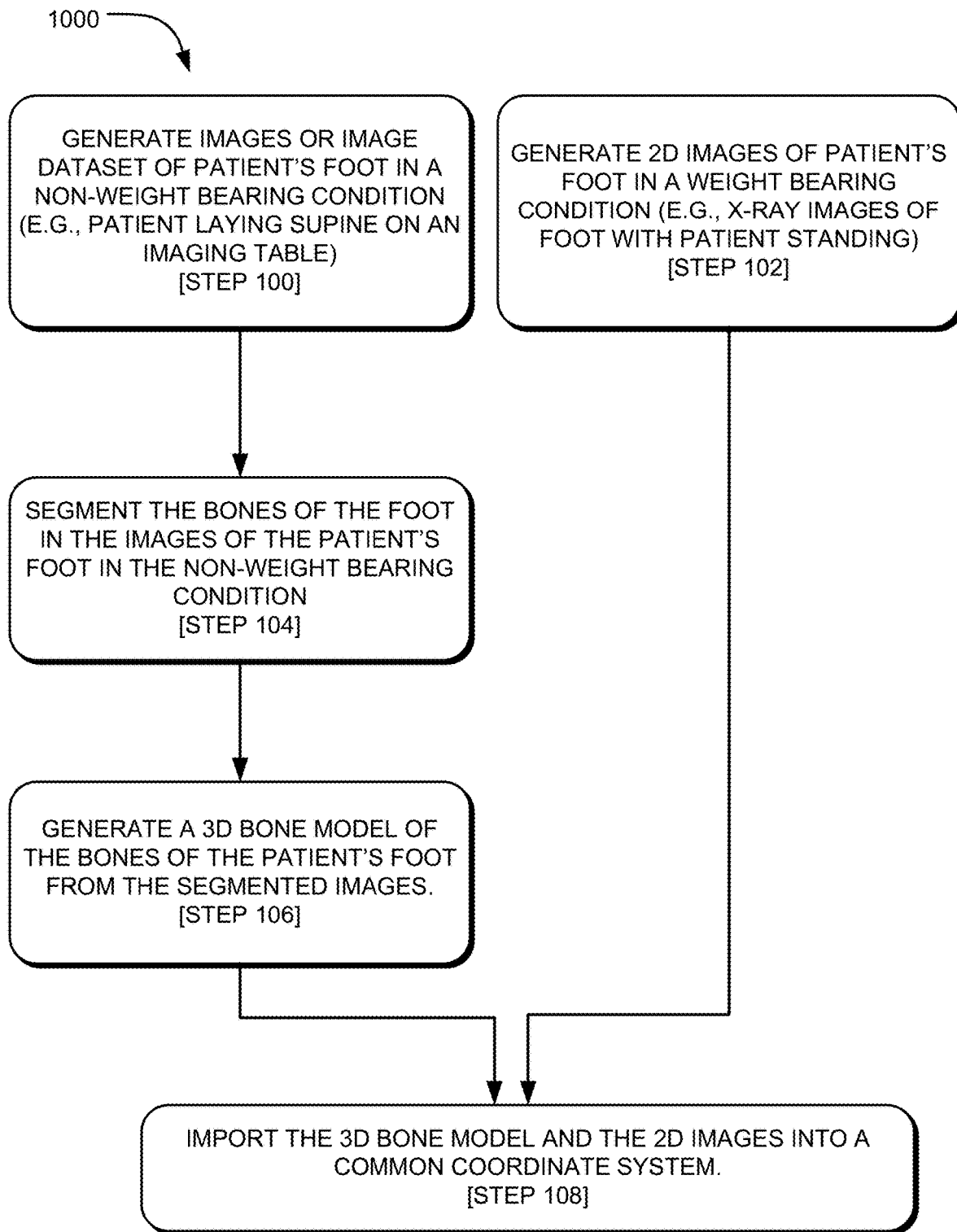
FIG. 1A through 1B are flowcharts depicting an exemplary method of pose estimation of a 3D bone model in a total ankle replacement procedure.

Aspects of the present disclosure involve mapping weight bearing conditions of the foot and leg from X-ray images obtained with a standing patient to the 3D bone model of the foot and leg obtained from CT images of the patient in a non-standing, supine position. Such mapping is beneficial in aligning the foot along its natural or weighted position with respect to the tibia.

And while the disclosure describes mapping weight bearing conditions of the foot from standing images to 3D bone models of the foot obtained from non-standing images, the disclosure also encompasses mapping weight bearing conditions of other bones and joints of the body including hips and knees, among other joints and bones making up the joints without limitation. For example, standing X-ray images of a patient's hip region or knee region may be acquired, as well as non-weight bearing images of the patient's hip region or knee region, respectively. 3D bone models may be generated of the patient's hip region or knee region, and the pose of the bones of the 3D bone models may be modified based on the poses of the bones in the standing X-ray images. In the case of mapping weight bearing conditions of an X-ray to a 3D bone model of a patient's hip, the standing and non-standing images may show different relationships between the ilium and the femur and tibia. Similarly, in the case of mapping weight bearing conditions of an X-ray to a 3D bone model of a patient's knee, the standing and non-standing images may show different relationships between the femur and tibia.

The following discussion includes three methods of positionally modifying the 3D bone models generated from CT images based on information from weighted pose of the foot and leg bones in the X-ray images. The three methods are: pose estimation via comparison of 2d image and 3d bone model in common coordinate system; pose estimation via 2d comparison of x-ray and plurality of bone model projections; and augmented pose estimation.

I. Pose Estimation Via Comparison of 2D Image and 3D Bone Model in Common Coordinate System The manual pose estimation method is where the 3D bone models of a patient's leg and foot bones (e.g., tibia, fibula, talus, calcaneus) obtained from segmenting the foot and leg from the CT images are imported into a 3D coordinate system of a computer along with X-ray images of the same patient's leg and foot. As discussed previously, however, the X-ray images depict a standing pose or orientation of the bones of the foot and leg. In certain instances, the 3D bone model in a first pose may be overlaid or superimposed on top of the X-ray image, which depict the bones in a different (standing) pose. Since the X-ray images are lateral views and anteroposterior views, the 3D bone models may be interchangeably shown in lateral views and anteroposterior views to match the X-ray images in the same lateral views and anteroposterior views, respectively. And the orientation of the individual bones of the bone model may be altered to match the pose of the bones in the standing X-ray images.

To begin, reference is made to FIG. 1A, which is a flowchart listing steps of an exemplary method 1000 of pose estimation of three-dimensional bone models in surgical planning a total ankle replacement procedure. As seen in the figure, step 100 of the method 1000 includes generating images (in the case of sequential images) or an image dataset (in the case of a continuous volumetric dataset produced, for example, via a helical CT scan) of a patient's foot in a non-weight bearing condition.

Figure 2:
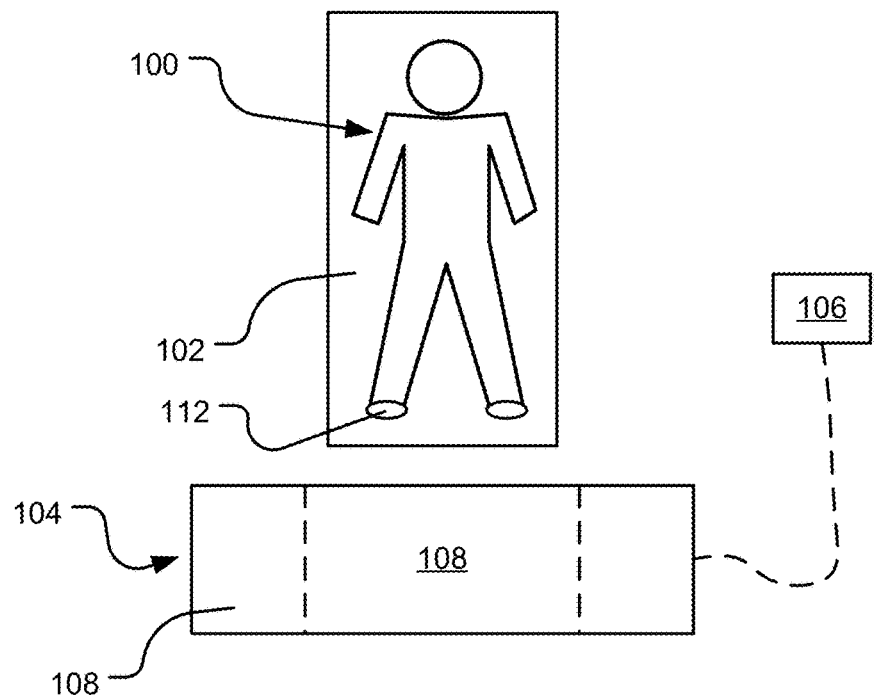
FIG. 2 is an overhead view of a patient laying supine on an imaging table proximate an image scanning machine.

Corresponding to step 100 of FIG. 1A, reference is made to FIG. 2, which is an overhead view of a patient 100 laying supine (i.e., on his or her back) on an imaging table 102 proximate an image scanning machine 104 (e.g., computed tomography (CT), magnetic resonance imaging (MRI), ultrasound) in communication with a computer 106. As seen in the figure, the imaging table 102 may be a motorized platform that is aligned with an opening 108 in a ring 110 of the image scanning machine 104. The imaging table 102 may be translated so a portion of the table 102 supporting the patient 100 extends into the opening 108 of the ring 110 of the machine 104. For example, in the case of an imaging procedure on the patient's leg and foot 112, the table 102 may be translated until the patient's leg and foot 112 is within the ring 110 of the machine 104. In the case of a CT image scanning machine 104, a scan of the patient may produce a volumetric dataset or individual slices (e.g., axial, coronal, sagittal). Most conventional CT image scanning machines 104 are helical computed axial tomography machines where the x-ray beam traces a helical path relative to the patient, as the patient is translated relative to the machine. The helical CT machines 104 produce a volumetric scan that can be reconstructed into sequential images with a defined spacing, which is a similar result to sequential scanning acquisition machines 104 that perform scans at a pre-defined spacing as the gantry moves the patient sequentially through the ring 110 of the machine 104. Helical CT machines 104 may be advantageous because a helical scan of the patient can be performed in seconds, whereas a sequential scan can take tens of minutes.

As the patient's leg and foot 112 is scanned via the scanning machine 104, the computer 116 stores the raw data obtained from the image scan, and may process the data so it is useable by a user (e.g., radiologist, engineer, surgeon). The raw data may be processed and stored as a Digital Imaging and Communications in Medicine ("DICOM") file. The DICOM file is a communication protocol and a file format for storing medical information, such as the volumetric dataset of the patient's foot, for example. Using a DICOM viewer program, the DICOM file can be opened and the data can be viewed in various forms. For example, volumetric data from a helical scan can be reconstructed into various two-dimensional ("2D") views such as axial, sagittal, and coronal views. The data may additionally or alternatively be processed into Digitally Reconstructed Radiographs ("DRR").

Figure 6:
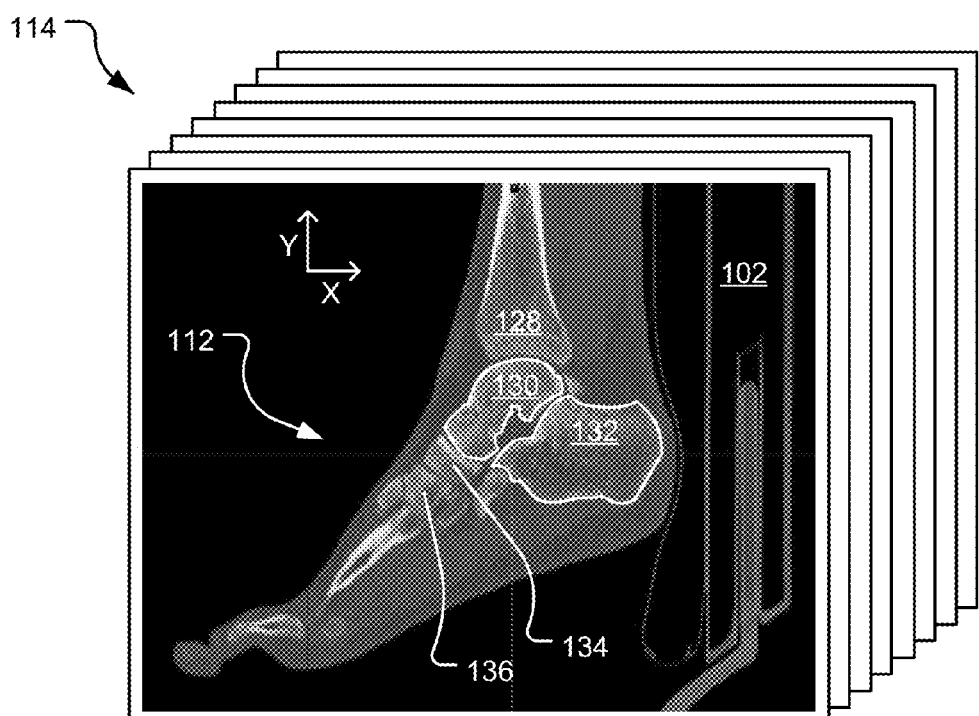
FIG. 6 is a sagittal image slice of a plurality of image slices taken of the patient's foot with the patient in the supine position (non-weighted condition), where the bones are segmented.

Upon processing of the raw data from the image scanning machine 104 via the computer 116, exemplary 2D images can be seen in FIG. 6, which specifically shows a stack 114 of scan or slice images 116 of the patient's leg and foot 112. In this example, the images 116 may be 2D images reconstructed from a volumetric dataset acquired via a helical CT machine 104 or from a CT machine 104 that acquired sequential images. As seen in FIG. 6, the images 116 are sagittal image slices 116 of the leg and foot 112. The entire stack 114 of image slices 116 may make up the entirety of the patient's leg and foot 112 from a medial side to a lateral side.

The images 116 of the patient's leg and foot 112 are with the patient lying on the imaging table 102 in a supine position. That is, the patient's leg and foot 112 is unweighted, or in a non-weight bearing condition. Thus, the images 116 taken with the imaging machine 104 show the bones of the leg and foot 112 in an uncompressed or non-load bearing fashion.

Step 100 may be described as a computer process that includes a step of receiving first patient bone data 116, 114 of a patient leg and foot 112 in a first pose. The first patient bone data 116, 114 may be generated via a first imaging modality such as CT or MRI. The first pose may include a position and orientation of the patient leg relative to the patient foot 112 as defined in the first patient bone data 116, 114.

Figure 3:
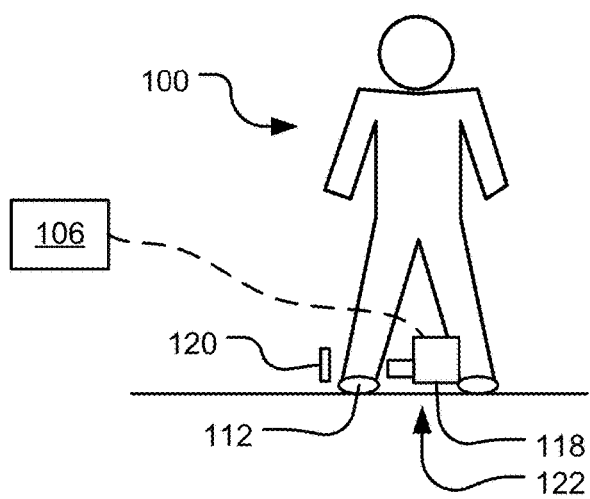
FIG. 3 is a front view of a patient standing and having a medial x-ray of the foot.

The images 116 of the patient's leg and foot 112 in a non-weight bearing condition are in contrast to X-ray images of the patient's foot in a weight bearing condition. Referring back to FIG. 1A, step 102 of the method 1000 may include generating two-dimensional ("2D") images of the patient's leg and foot in a weight bearing condition. To that end, reference is made to FIGS. 3 and 4, which depict, respectively, the patient 100 having a medial and an anteroposterior X-ray of the leg and foot 112 with the patient 100 in a standing position. As seen in FIG. 3, a generator 118 and a detector 120 of an X-ray machine 122 are positioned on either side of the foot 112 of the patient 100. The generator 118 is positioned on the medial side of the foot 112, and the detector 120 is positioned on the lateral side of the foot 112 in FIG. 3. Thus, the resulting 2D X-ray image 124 of the foot 112 in a medial or lateral view can be seen in FIG. 5A. In certain instances, a lateral 2D X-ray image of the patient foot 112 may also be generated (not shown).

Figure 4:
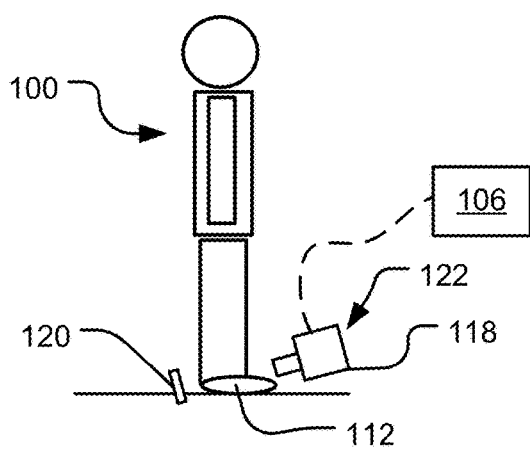
FIG. 4 is a side view of the patient standing and having an anteroposterior x-ray of the foot.

As seen in FIG. 4, the generator 118 is positioned in front of the foot 112 and the detector 120 is positioned behind the foot 112 so as to produce an anteroposterior ("AP") X-ray image of the foot 112. The resulting 2D X-ray image 126 of the foot 112 in the anteroposterior position can be seen in FIG. 5B. The images 124, 126 of the patient's foot 112 produced via the X-ray machine 122 depict the bones of the foot in a weighted condition since the X-rays were performed with the patient 100 standing. While X-rays of the foot 112 are described as being performed in the medial, lateral, and anteroposterior views, X-rays may be taken of the foot 112 in additional or alternative views without departing from the teachings of the present disclosure.

Step 102 may be described as a computer process that includes a step of receiving second patient bone data 124, 126 of the patient leg and foot 112 in a second pose. The second patient bone data 124, 126 may be generated via a second imaging modality that is different from the first imaging modality such as X-ray. The second pose may include a position and orientation of the patient leg relative to the patient foot 112 as defined in the second patient bone data 124, 126.

Referring back to the method 1000 in FIG. 1A, step 104 may include segmenting the bones of the patient's foot in the images of the foot in the non-weight bearing condition. As seen in FIG. 6, the individual bones (tibia 128, talus 130, calcaneus 132, navicular 134, cuneiforms 136, metatarsals, phalanges, fibula, etc.) of the leg and foot 112 may segmented along their respective bone boundaries in each of the images 116 of the stack 114. While FIG. 6 illustrates the calcaneus 132 and the talus 130 segmented along their respective bone boundaries (i.e., the white line around the perimeter of the bones) in a single image 116, all bones or only the bones relevant to the TAR procedure may be segmented in all of the images 116 of the stack 114. Thus, after the segmentation process of step 104 of the method 1000 of FIG. 1A, all images 116 of the stack 114 may include the bones of the foot 112 segmented along their respective bone boundaries.

Figure 7:
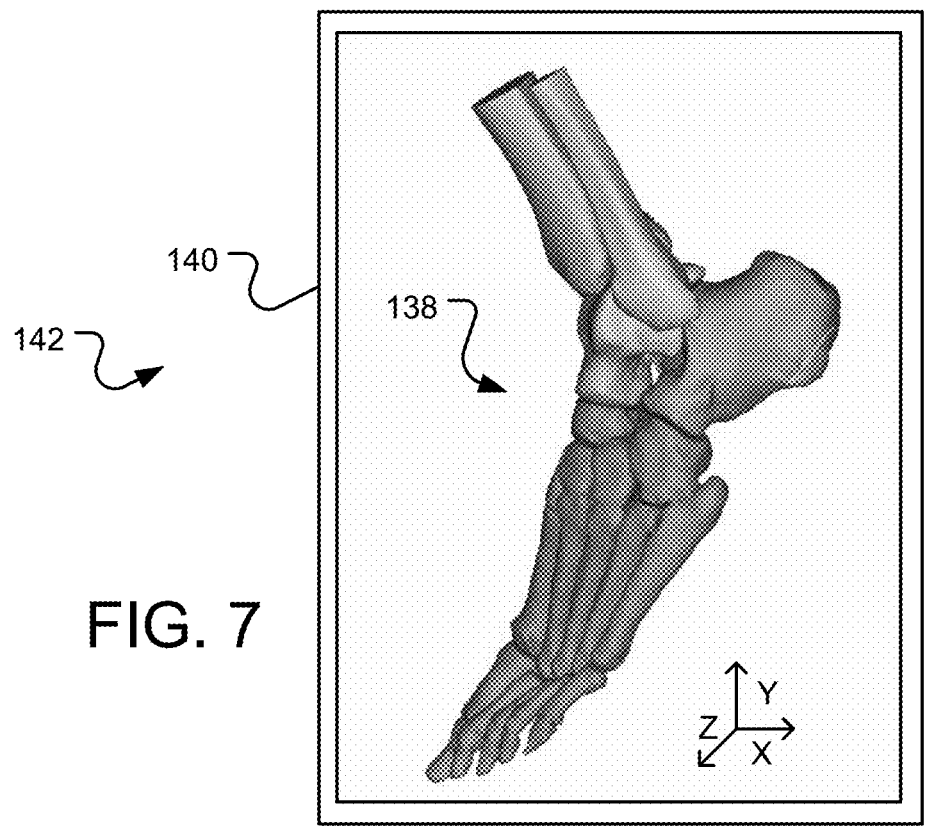
FIG. 7 is a lateral view of a three-dimensional bone model constructed from the plurality of image slices of the patient laying supine.

Next, step 106 of the method 1000 of FIG. 1A may include generating a three-dimensional ("3D") bone model of the patient's foot 112 from the segmented images 116 of the stack 116. An exemplary bone model 138 of the patient's foot 112 formed from the individually segmented bones in the images 116 of the stack 116, and displayed on a display screen 140 of a display device 142, may be seen in FIG. 7. Generation of the bone model 138 may be done via the computer 106 by interpolating a surface mesh between the spaces between the individually segmented images 116 to form a 3D surface profile approximating the surface contours of the bones of the patient's foot. As seen in FIG. 7, the bones of the foot 112 and the leg, including the tibia and fibula are at least partially generated into 3D form.

Exemplary computer programs for generating the 3D bone model 138 from the images 116 may include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org, among others.

Step 106 may be described as a computer process including a step of generating a three-dimensional (3D) bone model 138 of the patient leg and foot 112 from the first patient bone data 114, 116, where the 3D bone model includes a plurality of 3D bone models arranged in the first pose.

Figure 5A:
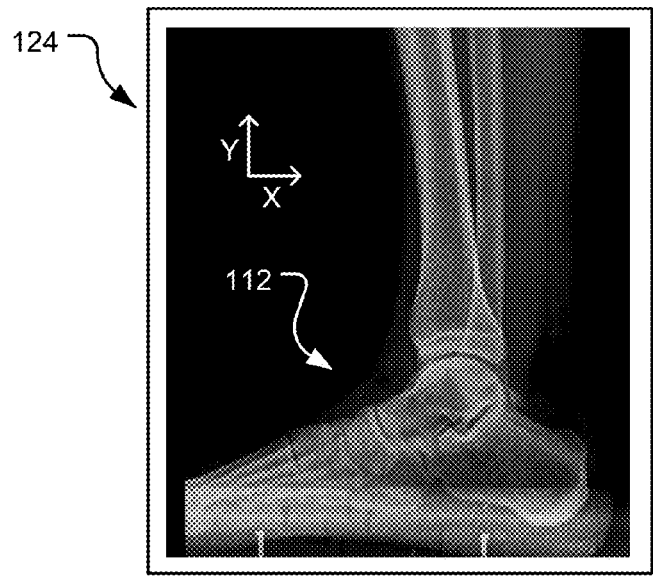
FIG. 5A is an example medial or lateral x-ray view of the patient's foot in a weighted condition.
Figure 5B:
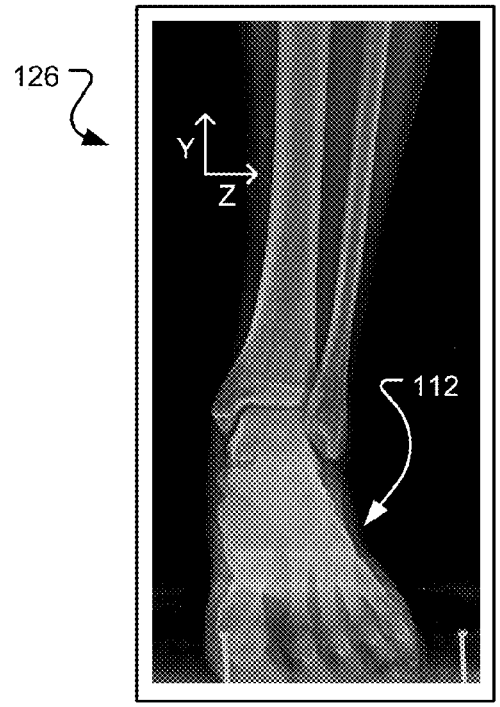
FIG. 5B is an example anteroposterior x-ray view of the patient's foot in the weighted condition.
Figure 8:
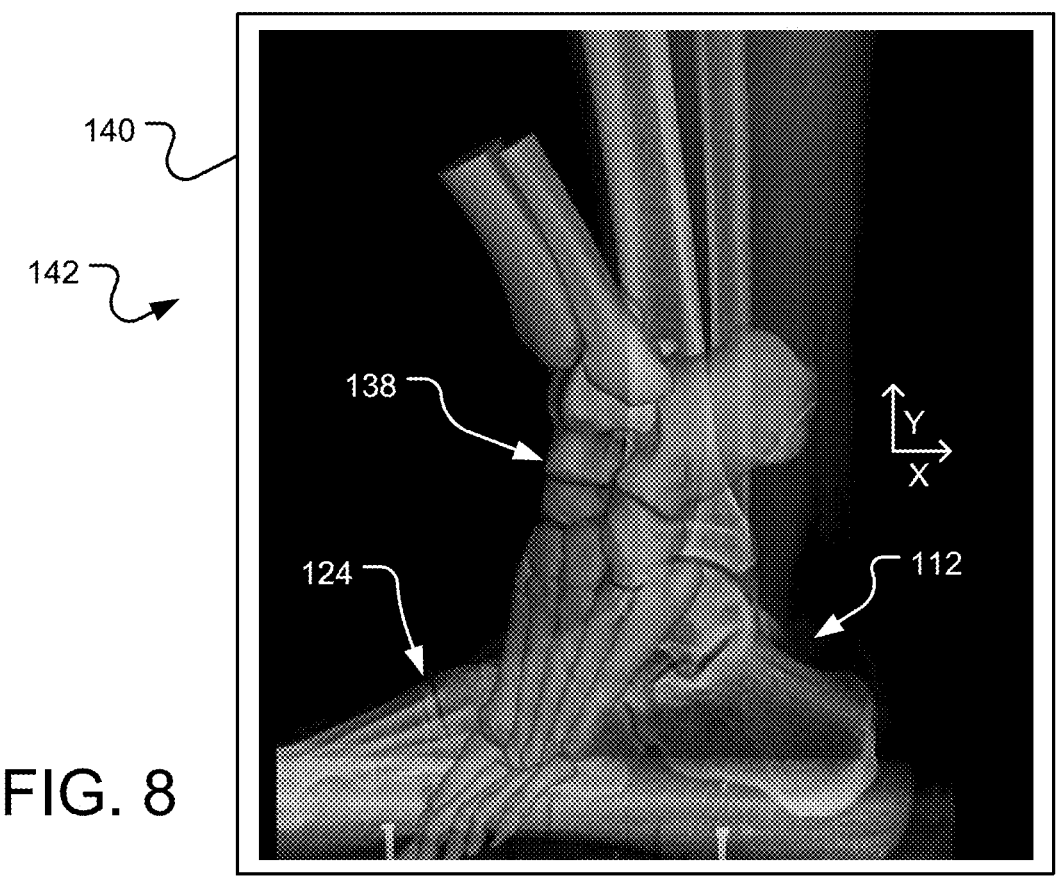
FIG. 8 is a lateral view of a 3D bone model overlaid on an X-ray of a patient's foot and leg bones, where X-ray depicts a standing pose of the foot and leg, and the 3D bone model depicts a non-standing pose of the foot and leg.

Referring back to FIG. 1A, step 108 of the method 1000 may include importing the 3D bone model 138 of FIG. 7 and the 2D images of FIGS. 5A and 5B into a common coordinate system. FIG. 8 illustrates the 3D bone model 138 and the 2D image 124 (medial or lateral view) of the patient's foot 112 in a common coordinate system (x,y,z). Since the 2D image 124 is a medial or lateral view in this example (planar views of the bones of the foot 112), the 3D bone model 138 may also be oriented in the same medial or lateral view. As seen in FIG. 8, the 3D bone model 138 is oriented in a lateral view to match a lateral 2D image 124.

Figure 1B:
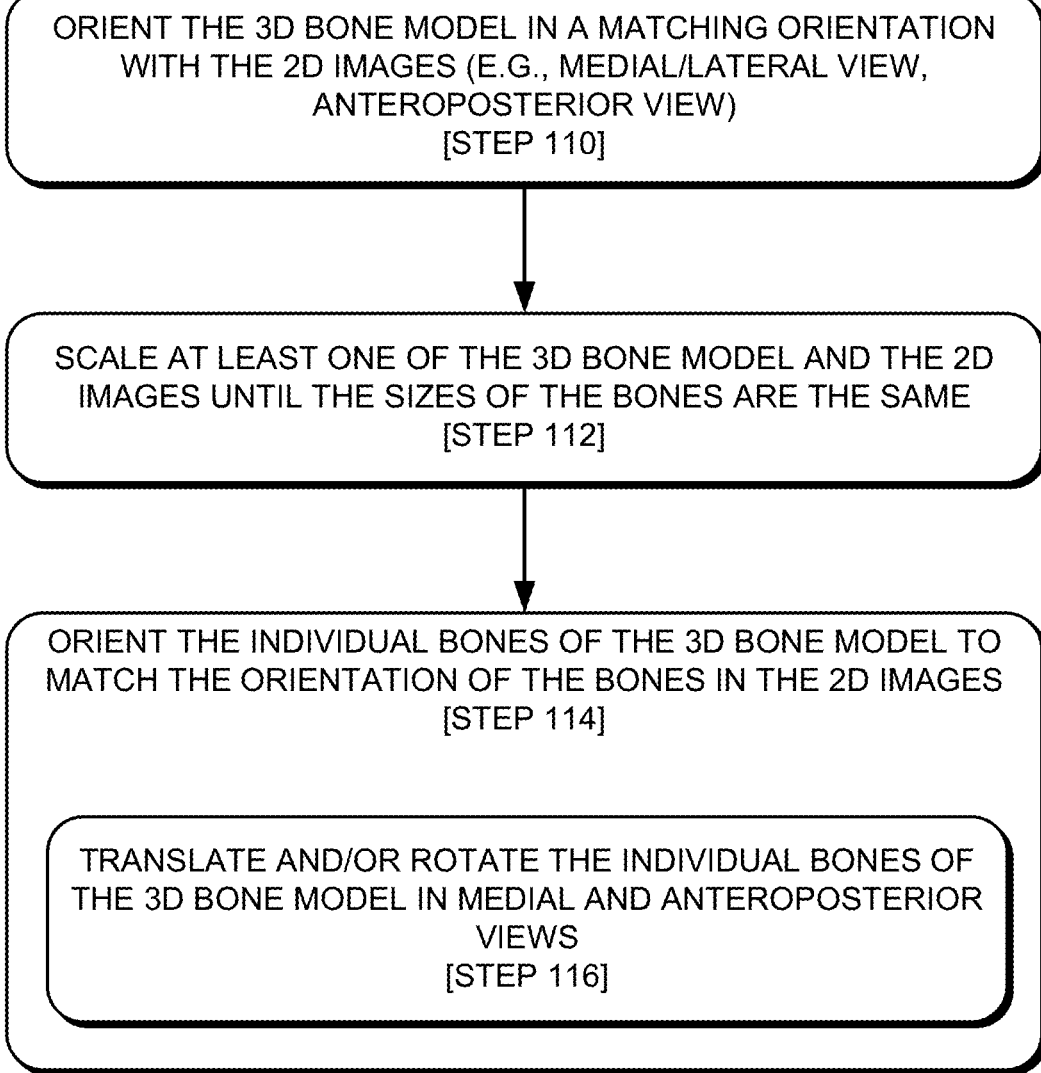

Referring to FIG. 1B, which is a continuation of the method 1000 of FIG. 1A, step 110 may include orienting the 3D bone model 138 in a matching orientation with one or both of the 2D images 124, 126. For example, as seen in FIG. 8, the 3D bone model 138 is oriented in a lateral view that matches the lateral 2D X-ray image 124. The 3D bone model 138 and the 2D image 124 are displayed on the display screen 140 of the display device 142 (e.g., computer 106, tablet). The 2D image 126 of the foot 112 in the anteroposterior view, of FIG. 5B, may not be shown in FIG. 8 because the image 126, which lies in a plane (y, z plane), is perpendicular to the plane (x, y plane) of the image 124 in FIG. 8. But, the orientation of the bone model 138 may be changed to the y, z plane such that the 2D X-ray image 126 of the foot 112 in the anteroposterior view is shown.

Step 112 of the method 1000 of FIG. 1B may also include scaling at least one of the 3D bone model 138 and the 2D images until the scales of the bones are the same. Since the 2D images 124, 126 are already the same size, the bone model 138 may be scaled to match the size of the bones in the 2D images 124, 126 with a single step. Alternatively, the scale of the 2D images 124, 126 individually or in combination may be scaled to match the size of the 3D bone model 138. The scaling may be performed manually or automatically. The scale of the 3D bone model 138 and the 2D image 124 are the same in FIG. 8.

Step 114 of the method 1000 of FIG. 1B may also include orienting the individual bones of the 3D bone model 138 to match the orientation of the individual bones of in the 2D images 124, 126. This step may include step 116, which may include translating and/or rotating the individual bones of the 3D bone model 138 in medial, lateral, and anteroposterior views to match the orientation of the bones in the corresponding 2D images 124, 126. This step may be described as a computer process including a step of modifying the 3D bone model 138 of the patient leg and foot 112 such that the plurality of 3D bone models are reoriented into a third pose that matches a particular arrangement of bones in the patient leg and foot in the second pose. In certain instances, the step of modifying the 3D bone model 138 may be manual, automatic, or partially manual and partially automatic.

Figure 9:
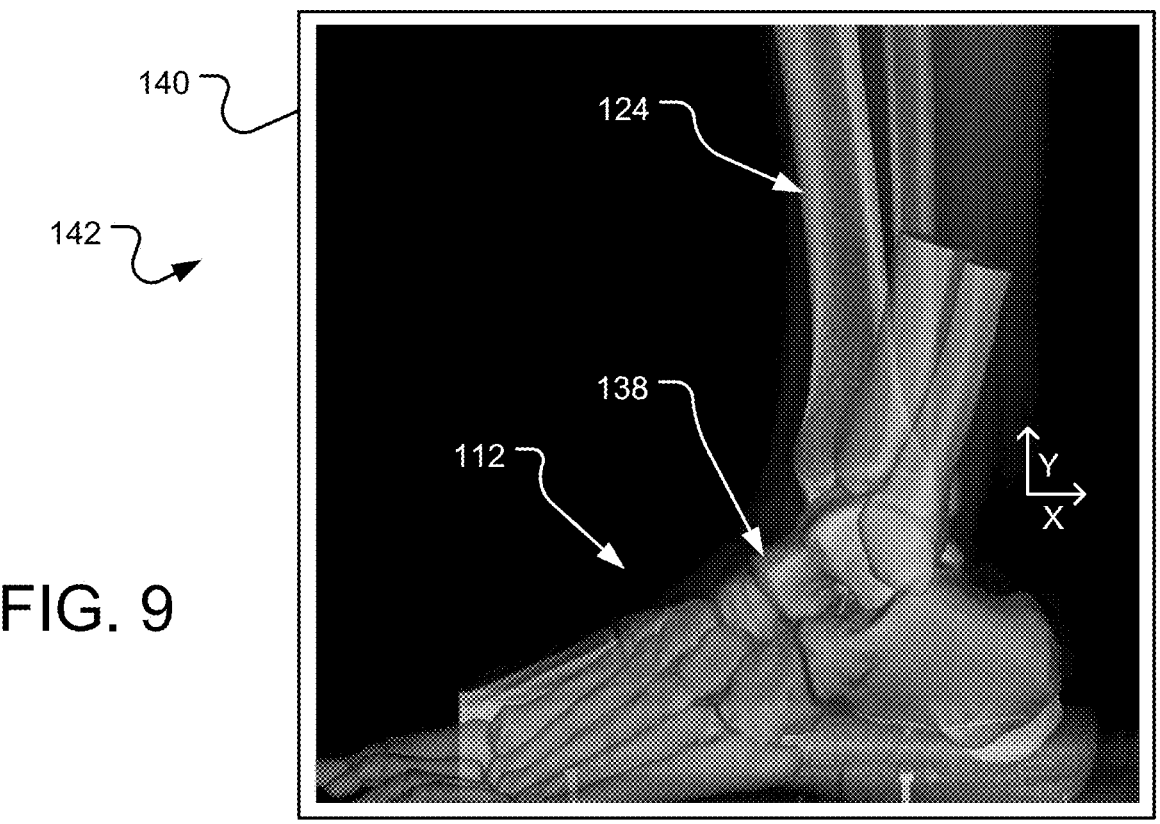
FIG. 9 is the lateral view of the 3D bone model and X-ray of FIG. 8, except the 3D bone model of the foot has been roughly aligned with the X-ray image.

As seen in FIG. 9, which is a view of the 2D image 124 of the foot 112 in the weighted condition overlaid with the 3D bone model 138 of the foot in the non-weighted condition, the bones of the foot in the bone model 138 have been rotated clockwise and translated in the y-direction until a proximal surface of the talus in the bone model 138 is coextensive or overlaps with the proximal surface of the talus in the 2D X-ray image 124. As seen in FIG. 9, the individual bones of the 3D bone model 138 have not yet been moved relative to each other. Instead, the entire set of bones forming the 3D bone model 138 have been roughly aligned with the bones of the foot 112 in the X-ray image 124.

Figure 10:
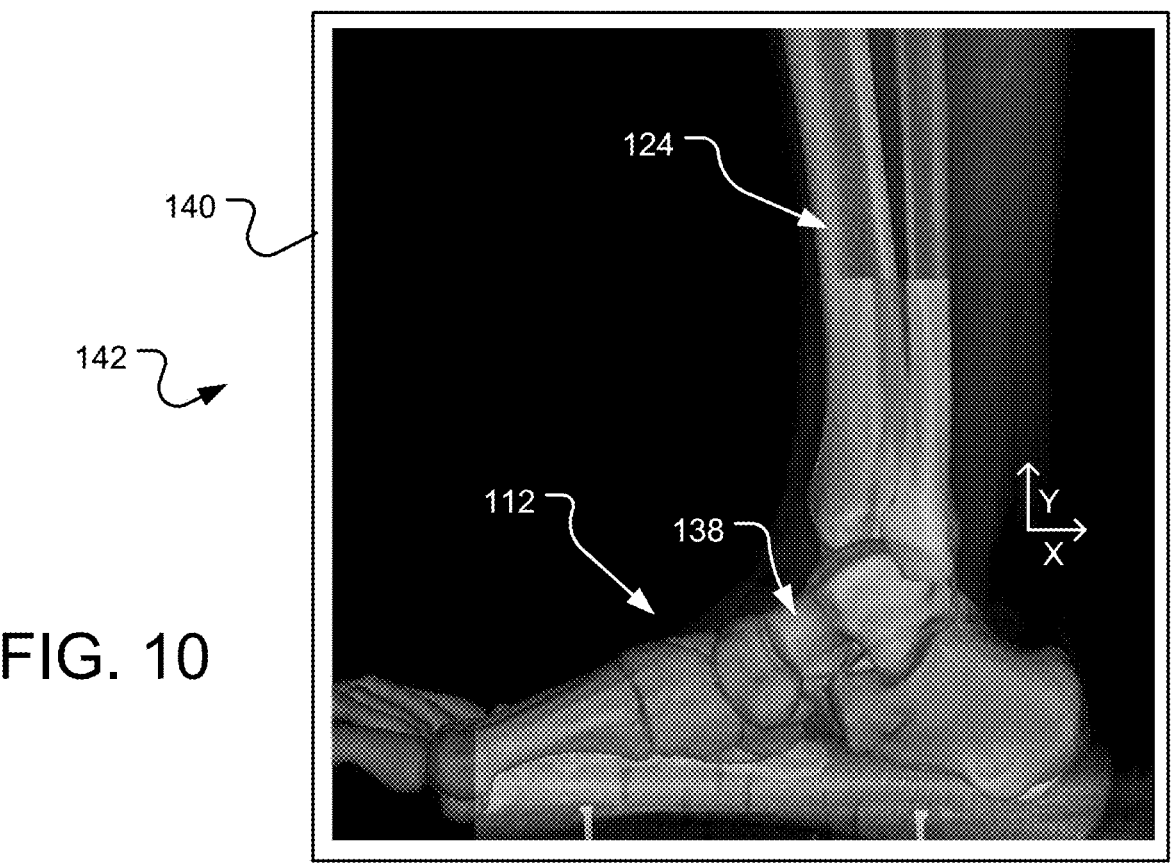
FIG. 10 is the lateral view of the 3D bone model and X-ray of FIG. 8, except the individual bones of the 3D bone model of the foot and leg (tibia, fibula) have been rotated and/or translated so as to align with the bones of the foot in the X-ray image.

Reference is made to FIG. 10, which is the same views of the 3D bone model 138 and 2D X-ray image 124 displayed on the display screen 140 of the display device 142 of FIG. 9, except the individual bones of the 3D bone model 138 have been translated and/or rotated relative to each other so as to match the pose of the bones of the foot 112 in the X-ray image. As seen in FIG. 10, an outline or projection of the bones of the bone model 138 have been adjusted or reoriented relative to each other so as to match the positioning/spacing orientation of the bones in the 2D X-ray image 124 in the medial view. The same process may take place for adjusting the orientation of the bones in the y, z plane with respect to the 2D X-ray image 126 of the foot 112 in the anteroposterior view, as well as other views including but not limited to the medial view, dorsal view, etc.

The 3D bone model 138 of the foot 112, in FIGS. 9 and 10, may be encircled by a rotation tool (not shown) indicating the computer 106 may rotate the selected 3D bone model of the foot within the particular plane to match the particular pose of the foot 112 in the X-ray image 124. The rotation tool may rotate the 3D bone models 138 about any axis (e.g., x,y,z) to align the models with the X-ray images. The GUI of the computer 106 may include a translation tool (not shown) for translating any of the bones of the bone model 138 in a particular direction (e.g., x, y, z). Particularly, the GUI may permit the translation tool 146 to move the bones of the bone model 138 in an x-direction or y-direction. On the GUI of the computer 106, there may be a selection drop down for switching each of the 3D bone models 138 between cuneiform, cuboid, metatarsals, calcaneus etc. Additionally, the GUI of the computer may also allow the switching between rotation, scale and translation modes.

The 3D bone models 138 and X-ray images 124, 126 may be iteratively translated, rotated, and/or scaled till the bone contour lines (outer most boundary as projected on a plane) align with each other. Additionally or alternatively, certain bone landmarks on the bone surface may be identified in each of the 3D bone models 138 and X-ray images 124, 126 and the landmarks may be positionally matched such that they align with each other. Instead of surface landmarks, a centroid of the 3D bone models may be identified and similarly identified in the lateral and anteroposterior views of the X-rays 124, 126, and the centroids can be matched so the models and X-rays align with each other.

In certain instances, accuracy of mapping the 3D bone models to the X-ray images may be improved by introducing pick able landmarks on the X-ray and the Bone mesh for correspondence.

Figure 11A:
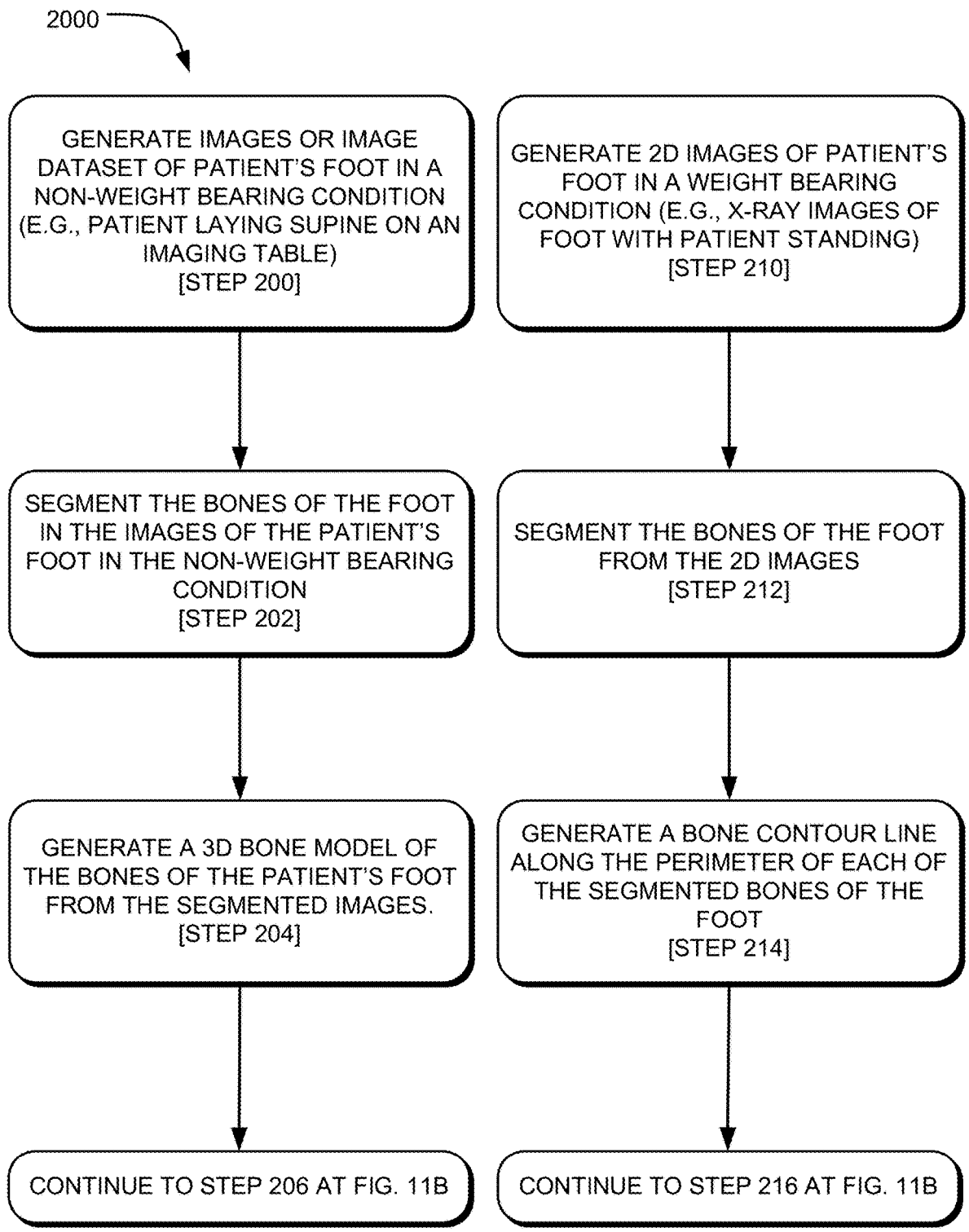
FIGS. 11A-11C are flowcharts depicting an exemplary method of pose estimation of a 3D bone model in a total ankle replacement procedure.

II. Pose Estimation Via 2D Comparison of X-Ray and Plurality of Bone Model Projections In the automated pose estimation, the mapping of the 3D bone models to the X-ray images may be fully or partially automated. One such method 2000 for automated pose estimation of a 3D bone model 138 may be seen in the flowchart of FIGS. 11A-11C. Referring to FIG. 11A, the method 2000 may include steps 200, 202, and 204, which are identical to steps 100, 104, and 106 of the method 1000 described in reference to FIG. 1A, among others. Thus, steps 200, 202, and 204 will not be described in detail; instead, please refer to the previous discussion of steps 100, 104, and 106 for a detailed description. Generally, step 200 may include generating images or an image dataset (e.g., CT images, MRI, ultrasound images) of the patient's foot 112 in a non-weight bearing condition such as, for example, with the patient 100 laying supine on a an imaging table 102. At step 202, the bones of the foot 112 as seen in the images or image dataset may be segmented (e.g., along the bone contour lines in sagittal, axial, or coronal images). At step 204, a 3D bone model 138 of the patient's foot 112 may be generated from the segmented images.

Step 210 of FIG. 11A is the same as step 102 of FIG. 1A; therefore, a detailed discussion of this step will not be included for the method 2000 in FIG. 11A. Please refer to the details of step 102 regarding the specifics of step 210. Generally, step 210 may include generating 2D X-ray images 200 (as seen in the lateral X-ray view of FIG. 12A and the medial X-ray view of FIG. 12B) of the patient's foot 112 in a weight bearing condition (e.g., standing X-rays). Medial, lateral, and anteroposterior views (seen in FIG. 5B), among others, may be generated. The X-ray images 200 of FIGS. 12A and 12B are illustrative and may be labeled as: right foot, lateral-to-medial view, and right foot medial-to-lateral view; or left foot, medial-to-lateral view, and left foot lateral-to-medial view, respectively, as it can be difficult or impossible to determine the views of X-rays without labeling.

Step 212 of FIG. 11A may include segmenting the individual bones of the foot 112 in the 2D X-ray images 200. As seen in FIG. 12A, the talus 202 and the calcaneus 204 are segmented from the 2D X-ray image 200 in the lateral view, and the same bones are segmented from the 2D X-ray image 200 in the medial view of FIG. 12B. Segmentation may also take place with a 2D X-ray image 200 in an anteroposterior view (not shown), among others.

Figure 12A:
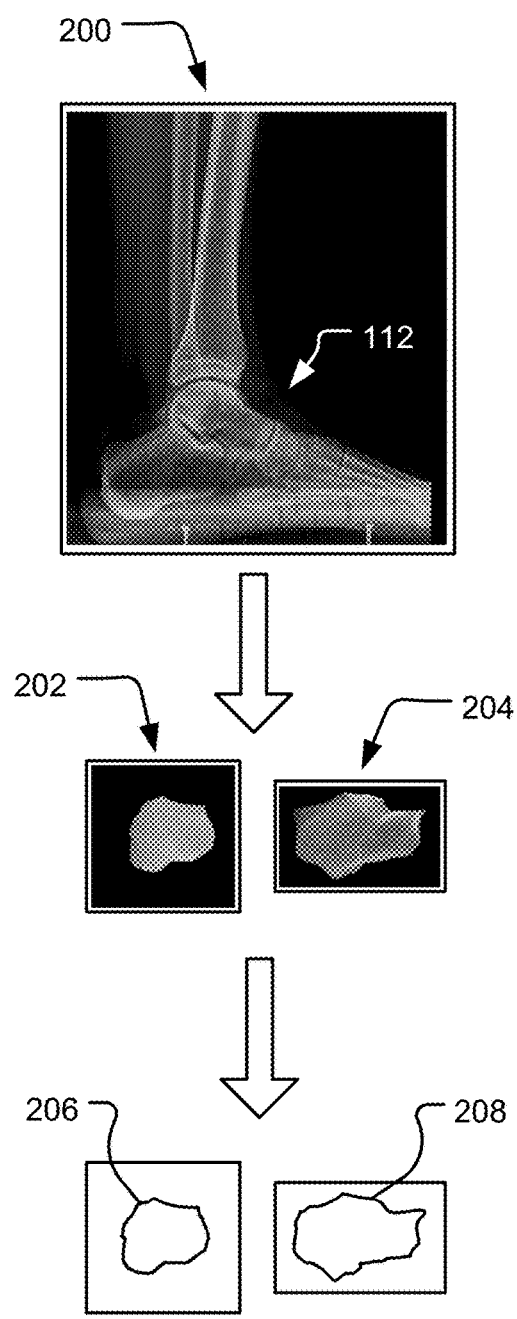
FIG. 12A depicts a lateral-to-medial X-ray image of a patient's foot, segmented bones from the X-ray image, and a perimeter contour line defined from the segmented bones.
Figure 12B:
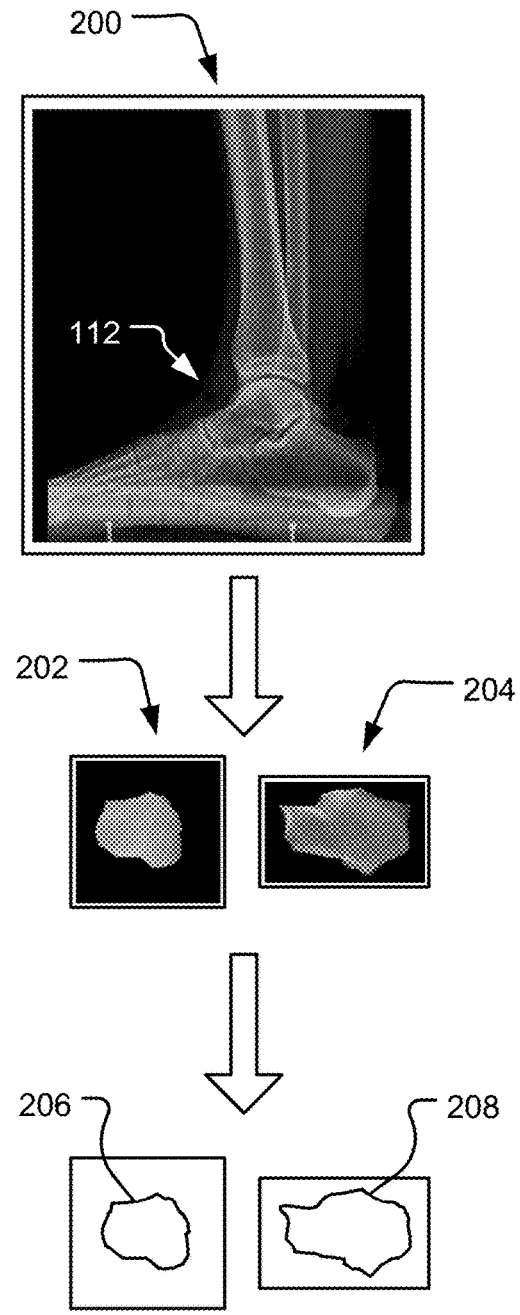
FIG. 12B depicts a medial-to-lateral X-ray image of a patient's foot, segmented bones from the X-ray image, and a perimeter contour line defined from the segmented bones.

In FIGS. 12A and 12B, only the talus 202 and calcaneus 204 are shown segmented, but other bones of the foot 112 including the tibia, navicular, cuneiforms, metatarsals, and phalanges, among others, may be segmented. The bones of the talus 202 and calcaneus 204 are exemplary illustrations, but the method 2000 is intended to include the segmentation or additional or alternative bones of the foot 112 depending on the bones desired to be estimated in their pose.

Following segmentation in step 212, step 214 of FIG. 11A may include generating a bone contour line along the perimeter of each of the segmented bones of the foot 112. As seen in FIGS. 12A and 12B, beneath the segmented talus 202 is a contour line 206 defining a perimeter of the segmented talus 202, and beneath the segmented calcaneus 204 is a contour line 208 defining a perimeter of the segmented calcaneus 204. The perimeter contour lines 206, 208 represent an outer shape of the bones of the talus 202 and calcaneus 204 in their particular pose (position and orientation) when standing in the X-ray image 200.

Figure 11B:
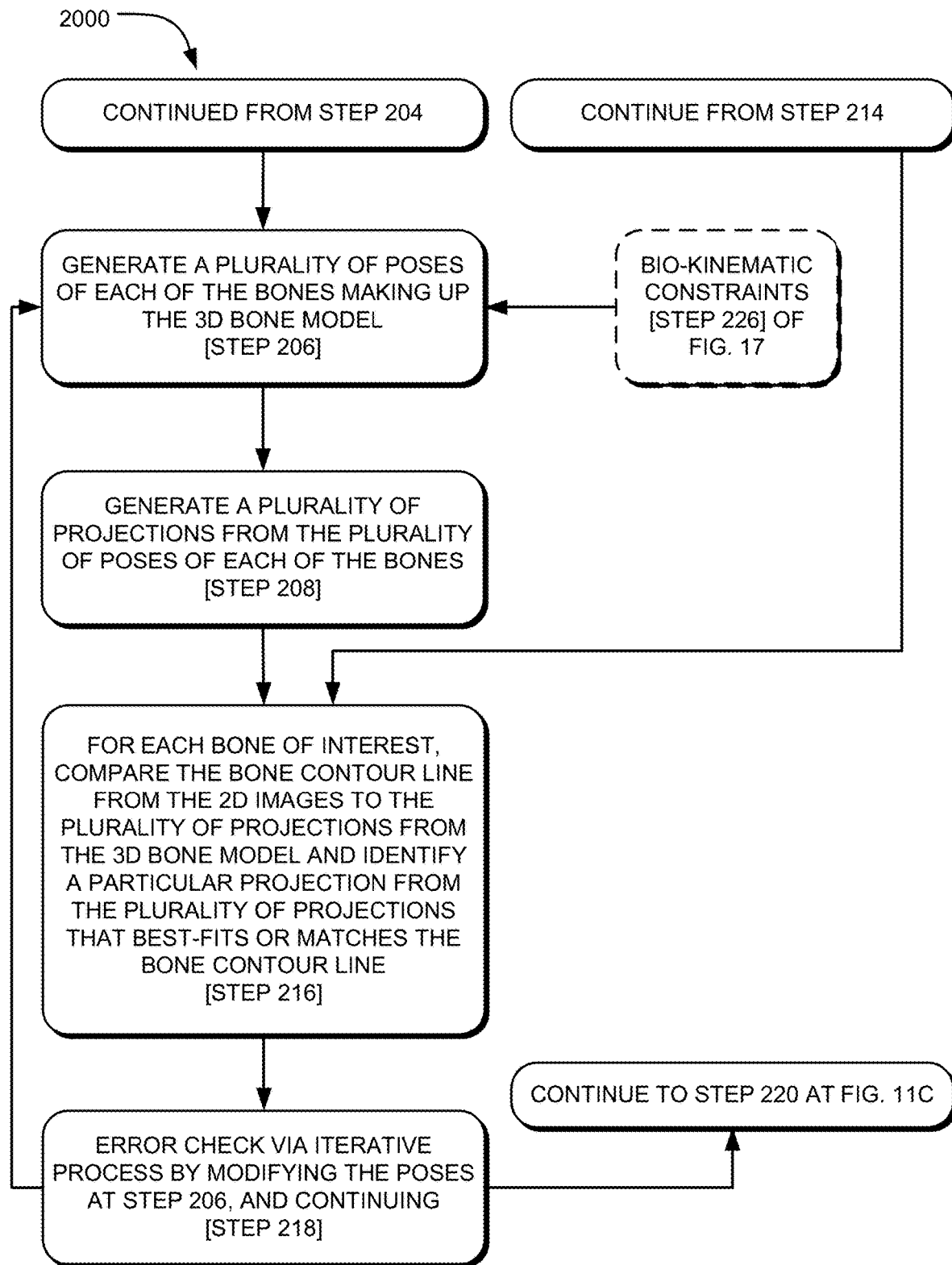

Turning back to the method 2000 as seen in FIG. 11B, and continuing from step 204, step 206 may include generating a plurality of poses of each of the individual bones making up the 3D bone model 138. FIGS. 13A, 13B, and 13C illustrate a 3D object 210 such as the individual bones making up the 3D bone model 138 of the foot in various poses, each having a different pose. FIG. 13A shows the object 210a in a first pose, FIG. 13B shows the object 210b in a second pose, and FIG. 13C shows the object 210c in a third pose. As described herein, pose refers to the position and orientation of an object in space. Therefore, it can be seen in FIGS. 13A, 13B, and 13C that the 3D objects 210a, 210b, 210c are in different rotation orientations relative to each other, each having been rotated along various axes. The 3D objects 210a, 210b, 210c may represent the individual bones of the 3D bone model 138 having been generated in a plurality of poses. Since there are many bones of the foot 112, and there are a near infinite number of poses for each of the bones of the foot 112, it is most efficient to describe the objects 210a, 210b, 210c as representing the plurality of poses of the bones of the foot 112.

In certain instances, a certain number of finite poses of each of the bones of the foot 112 may be generated. In certain instances, one hundred different poses of each of the bones of the foot 112 may be generated. In certain instances, five hundred different poses of each of the bones of the foot 112 may be generated. In certain instances, one thousand different poses of each of the bones of the foot 112 may be generated. In certain instances, the poses of each of the bones of the foot 112 can be changed in any one or multiple of the six degrees of freedom (three translations and three rotations). The smaller the differences among the poses (e.g., a change of 1 degree of rotation on an axis for each different pose), the higher the number of poses that will be generated. In contrast, the larger the differences between the poses (e.g., a change of 10 degrees of rotation on an axis for each different pose), the fewer the number of poses that will be generated.

Step 216 of FIG. 11B may include generating a plurality of projections from the plurality of poses of each of the bones of the foot 112. As seen in FIGS. 14A, 14B, and 14C, a projection (i.e., in a plane, in 2D) or outline of the perimeter 212 of each of the plurality of poses of the bones (or object 210 as seen in FIGS. 13A, 13B, and 13C) is generated. As seen in FIGS. 14A, 14B, and 14C, the projections 212a, 212b, 212c of the poses of the objects 210a, 210b, 210c are different for each pose, where the first pose of the object 210a in FIG. 13A yields the projection 212a in FIG. 14A. Similarly, the second pose of the object 210b in FIG. 13B yields the projection 212b in FIG. 14B, and the third pose of the object 210c in FIG. 13C yields the projection 212c in FIG. 14C.

Referring back to the method 2000 of FIG. 11B, step 216 may include a comparison step that includes comparing, for each bone of the foot 112 of interest, the bone contour line as determined from the 2D X-ray images 200 (contour line 206 for the talus, and contour line 208 for the calcaneus in FIGS. 12A and 12B) to the plurality of projections (projections 212a, 212b, and 212c in FIGS. 14A-14O) as determined from the 3D bone model 138, and identifying a particular projection from the plurality of projections 212a, 212b, 212c that best-fits or most closely matches the bone contour line.

Figure 15:
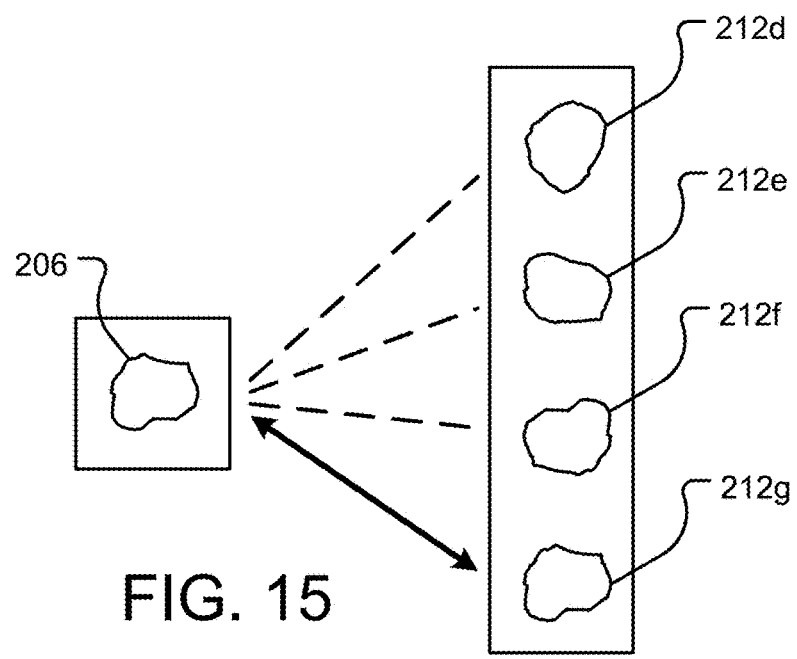
FIG. 15 depicts a comparison of a 2D perimeter contour line of a bone with a plurality of projections of poses of a bone from a 3D bone model.

FIG. 15 illustrates step 216 of the method 2000. As seen in the figure, the talus contour lines 206 as identified from the 2D X-ray images 200 is compared to an example plurality of projections 212d, 212e, 212f, and 212g, and a particular one of the plurality of projections 212g is identified as being the best-fit or closest match in shape and orientation. This comparison step 216 may include a shape matching algorithm that compares the shape and area within its boundary of each of the plurality of projections 212d-g to the shape and area within the boundary of the talus contour line 206. The particular projection 212g of the plurality of projections 212d-g that most closely matches the values of the talus contour line 206 is identified as the best-fit or most closely matching.

Each of the plurality of projections 212 may be sampled radially in the form of a shape context. And the data for each of the plurality of projections 212 may be compared with the shape context of the contour line 206.

The comparison and identification step 216 may include employing a Jaccard similarity coefficient for comparing the similarity and diversity contour line as determined from the 2D X-ray image to each of the plurality of projections as determined from the 3D bone model 138. In comparing the contour line 206 to each of the projections 212d-g, as seen in FIG. 15, a Jaccard similarity coefficient may be assigned to each comparison. The assigned coefficient can be used to determine which pair is the most similar. An example Jaccard similarity measurement may be defined as: Jaccard Similarity J (A, B)=|Intersection (A, B)|/|Union (A, B)|.

An example shape matching algorithm that may be employed in the method 2000 for comparing and identifying the particular projection that most closely matches the contour line as determined from the 2D X-ray images 200 may be seen in the following document, which is hereby incorporated by reference in its entirety: "A Comparison of Shape Matching Methods for Contour Based Pose Estimation" by Bodo Rosenhahn, Thomas Brox, Daniel Cremers, and Hans-Peter Seidel (https://vision.in.tum.de/_media/spezial/bib/rosenhahn_iwcia06.pdf).

Step 216 may be employed for each individual bone of interest. That is, while FIG. 15 only depicts the talus, step 216 may be employed for additional or alternative bones including the tibia, calcaneus, navicular, cuneiforms, metatarsals, phalanges, etc.

Referring back to FIG. 11B, the method 2000 at step 218 may include error checking via an iterative process to determine if there are any additional poses that provide a better-fit than the particular pose identified from the plurality of poses. Step 218 may include modifying the plurality of poses 210 and projections 212, and running the comparison and identification step of step 216 again to see if there are better-fit poses.

Figure 11C:
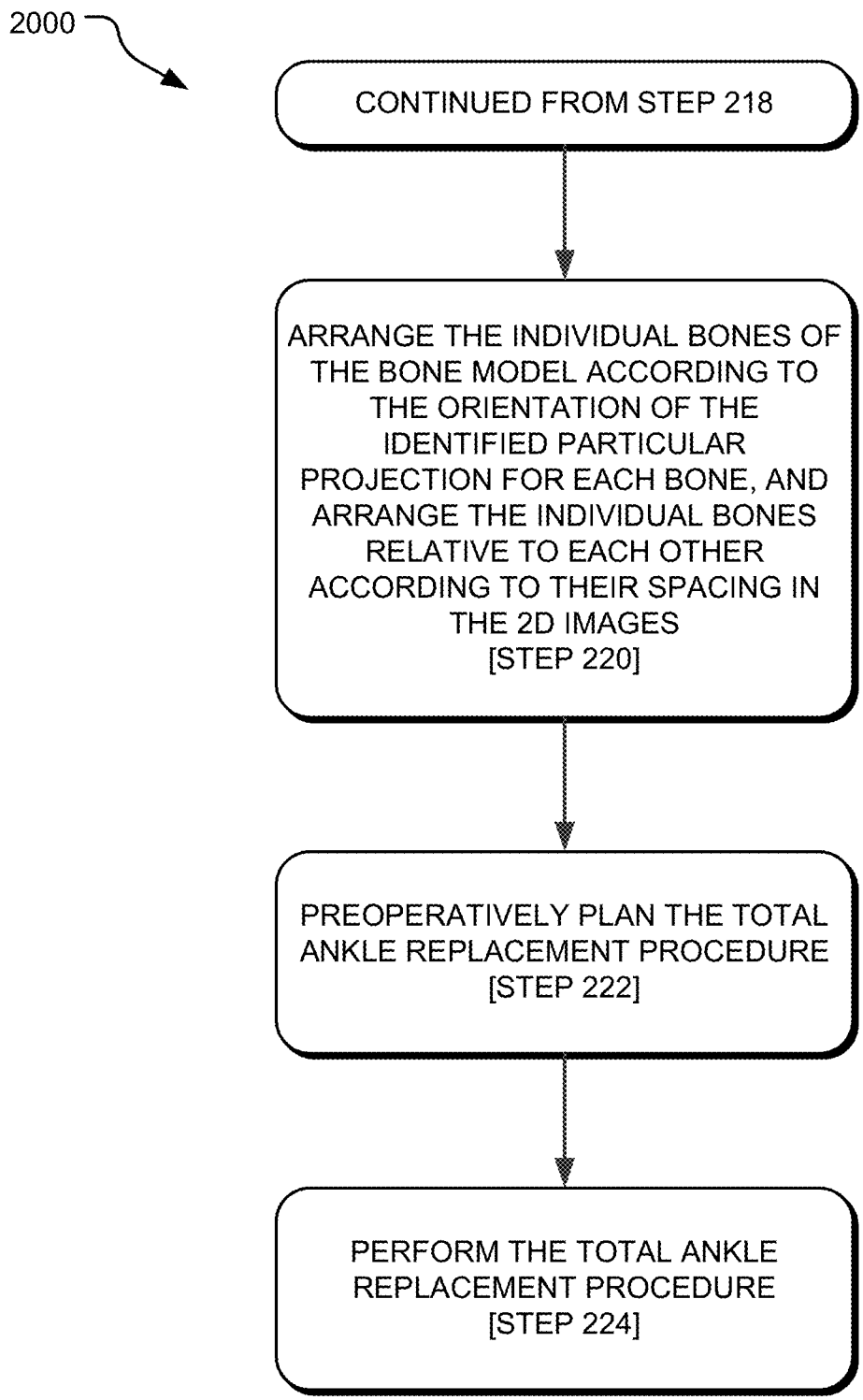

Once the iterative process has ran and the best-fitting projections have been determined, the individual bones of the bone model 138 may be arranged according to the orientation of the identified particular projection for each of the bones, and the individual bones of the bone model 138 may be arranged relative to each other according to their spacing in the 2D X-ray images 200, as seen in step 220 of FIG. 11C.

Stated differently, each of the particular projections identified as being the best fit to the contour lines determined from the 2D X-ray images 200 determines the orientation of the individual bones of the bone model 138. Step 220 may include arranging the individual bones of the bone model 138 according to their respective particular projection that was identified as the best fit with the contour lines determined from the 2D X-ray images 200.

Once the bones of the bone model 138 are arranged according to step 220, the bone model 138 is in a pose that matches or replicates a weighted condition of the foot 112 as it appeared in the 2D X-ray images 200.

Referring to FIG. 11C, the method 2000 may additionally include preoperatively planning the TAR procedure, at step 222. This step may include determining resection placement, resection depth, implant placement, implant depth, implant type and size, and surgical approach, among other parameters.

Step 224 of the method 2000 may then include performing the TAR procedure according to the preoperative plan at step 222. This may include sedating the patient, creating an incision into the patient's skin, resecting bone, implanting a fixation device or implant, and closing the incision, among other steps of a TAR procedure.

Referring back to FIG. 11C, the method 2000 may include, at step 226, applying bio-kinematic constraints to the generation of the plurality of poses for each of the bones making up the 3D bone model 138. The bio-kinematic constraints may limit the number of poses generated or the number of projections that are ultimately generated at step 208. The bio-kinematic constraints may limit the poses to those that are bio-kinematically relevant, whereas such poses that are not bio-kinematically relevant will not be generated, or will be discarded.

Figure 16:
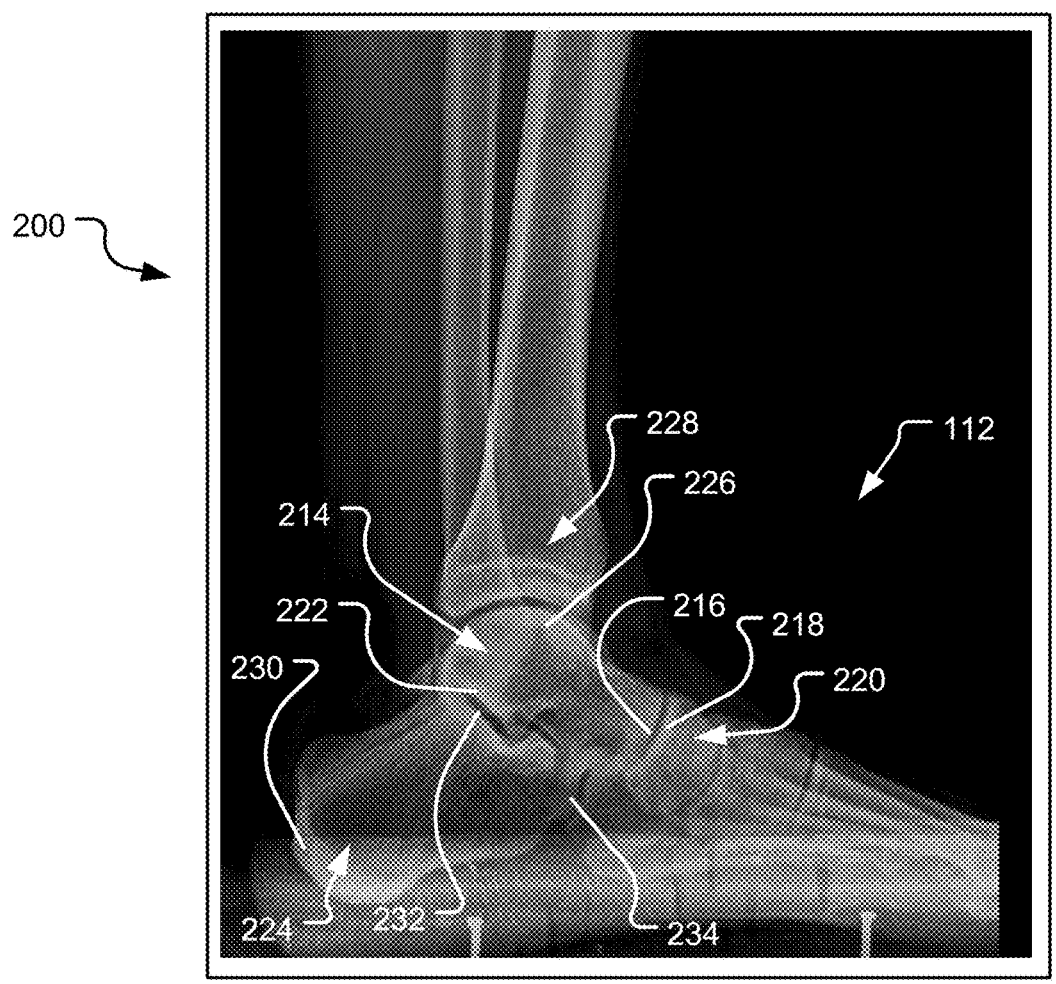
FIG. 16 depicts a lateral-to-medial or medial-to-lateral X-ray image of a foot including an identification of various landmarks therein.

In certain instances, the bio-kinematic constraints may include orientation guidelines for each bone as it relates to surrounding bones given a known view (e.g., lateral, medial, anteroposterior). That is, as seen in FIG. 16, which is a lateral-to-medial or medial-to-lateral X-Ray image 200 of the right foot 112, the talus 214, for example, includes a convex head 216 that articulates with a concave articular surface portion 218 on the superior surface of the navicular 220. The talus 214 also includes a large posterior facet 222 abutting the calcaneus 224, and a large superior articular surface (talar dome) 226 for abutting the inferior aspect of the tibia 228. Thus, if the view is known (e.g., lateral, medial, AP), certain constraints can be built into the system that exclude poses that are not relevant. For example, in a lateral view of the foot as seen in FIG. 16, certain parts of the bones may be identified in relevant bones. For the calcaneus 224, the calcaneal tuberosity 230, the posterior facet 232, and facet for cuboid 234 may be identified in the X-Ray image 200 or the segmented image of the calcaneus (not shown). For the talus 214, the talar dome 226, and head 216 may be identified in the X-Ray image 200 or the segmented image of the talus (not shown). For the navicular 220, the superior articular surface 218 for abutting the talus head 216 may be identified in the X-Ray image 200 or the segmented image of the navicular (not shown).

Once these points are identified on the relevant bones, certain poses can be eliminated that do not meet the bio-kinematics of the foot. For instance, the calcaneal tuberosity 230 must be at a left-most position in a lateral view of the right foot. The calcaneal posterior facet 232 generally faces oppositely of the calcaneal tuberosity 230, and abuts the talus 214. The calcaneal facet for the cuboid 234 is generally in a far right position in the lateral view of the right foot. For the talus 214, the talar dome 226 is generally oriented upwards, facing the distal tibia 228. And the talar head 216 generally faces to the right in the lateral view of the right foot. For the navicular 220, the superior articular surface 218 generally faces to the left in the lateral view of the right foot.

All this information can be used to constrain the poses generated at step 206 by eliminating poses that have, for example: the calcaneal tuberosity 230 at a far right position in a lateral view of the right foot 112; the calcaneal facet for the cuboid 234 that faces left; talar dome 226 facing downward or to the right; talar head 216 facing left; and superior articular surface 218 of the navicular 220 facing right; among others.

In certain instances, the 3D bone model 138 may be modeled using landmarks. For instance, the articular surfaces of the bones may be identified and the poses from step 206 may be limited to orientations that require the articular surfaces to oppose each other and be a certain distance from each other. Certain motion of the joints may also be used as constraints. For instance, the forefoot may be modeled as a hinge joint, and the talocrural joint can be modeled as a hinge joint with rotation axis about the line on the superior point of lateral and medial malleolus. Thus, certain poses that do not permit such rotation about the rotation axis may be eliminated.

Figure 17:
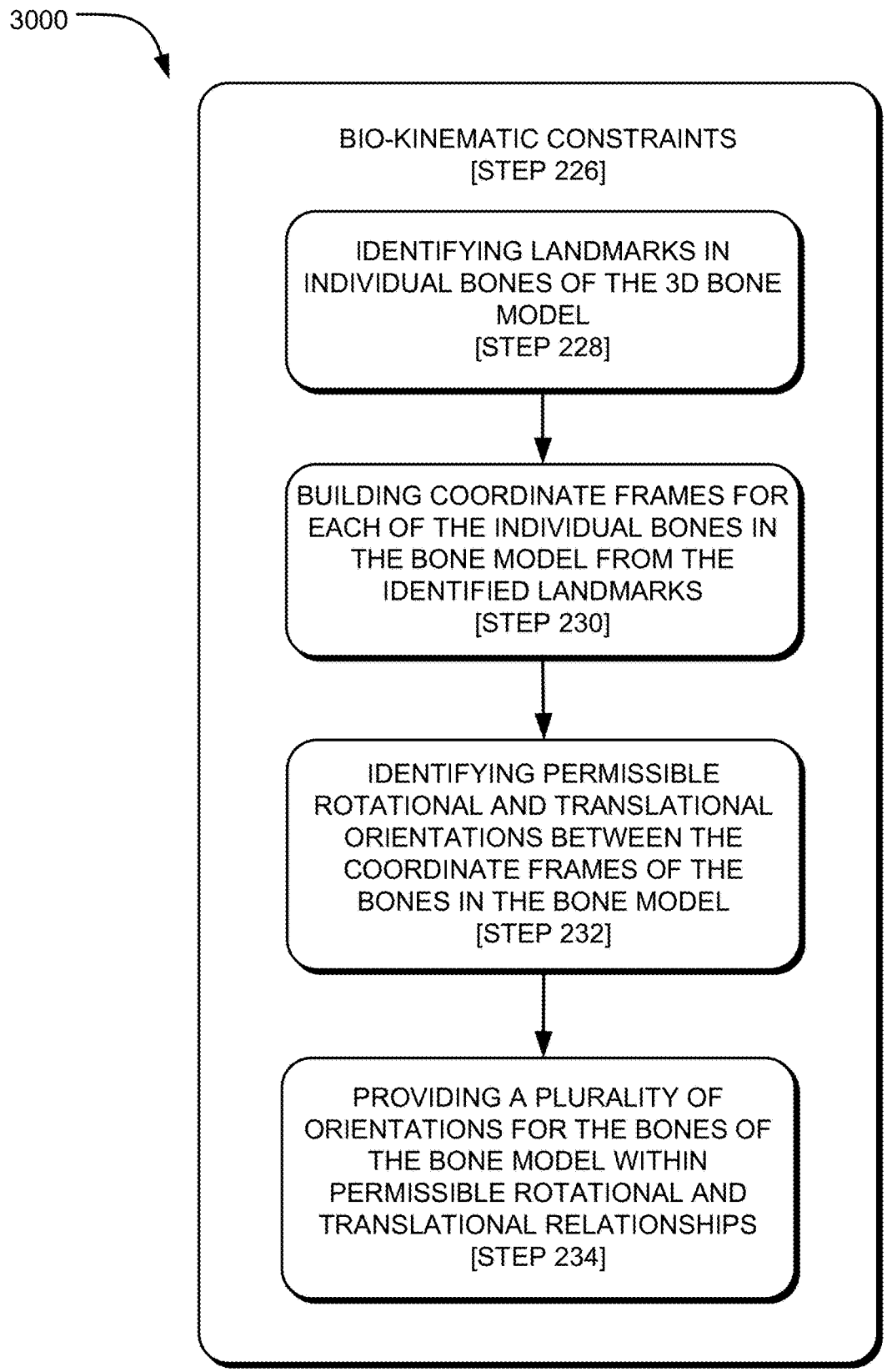
FIG. 17 is a flowchart depicting an exemplary method of constraining available poses for pose estimation using biokinematics of the foot.

FIG. 17 is a flowchart depicting an exemplary method 3000 for constraining the poses of step 206 using bio-kinematics (step 226). The method 3000 may include, at step 228, identifying landmarks in each of the individual bones of the 3D bone model 138. This step may include performing a topological data analysis ("TDA") to extract information from the dataset associated with each bone of the bone model 138. Next, at step 230, the method 3000 may include building coordinate frames for each of the bones in the bone model 138 from the identified landmarks of step 228. At step 232, the method 3000 may further include identifying permissible relationships (e.g., rotational orientation, translational orientation) between the coordinate frames for each bone of the bone model 138. At step 234, the method 3000 may include providing a plurality of orientations of the bones within permissible rotational and translational relationships for the generation of poses at step 206.

III. Augmented Pose Estimation

Another method of mapping the 3D bone models 138 to the X-ray images may include an augmented pose estimation, which may be a combination of manual and automated procedures. For instance, instead of running a contour matching algorithm as described in Section II. on a complete set of the bones of the leg and foot, the contour matching algorithm may be limited to certain bone structures, such as the fibula, tibia, talus, and, calcaneus. The remaining bones of the foot may be extrapolated from the resulting pose of the fibula, tibia, talus and calcaneus.

In certain instances, a user may manually map bone contour surfaces or landmarks on the individual bones of the 3D bone model 138 to corresponding points on the X-ray images, as described in Section I. Then, the user may perform an automation step (as in Section II) to optimize the pose further on particular bone structures. In this way, the user provides a "rough" estimate of pose, and the automation process fine-tunes the original "rough" estimate of pose.

In sum, the above described techniques may be used to estimate absolute pose of a foot 112 in anteroposterior, lateral, and medial views with respect to tibia and relative bone positions in the foot 112. These methods may improve accuracy in deformity assessment and hence correction for TAR procedures.

IV. Example Computing System

Figure 18:
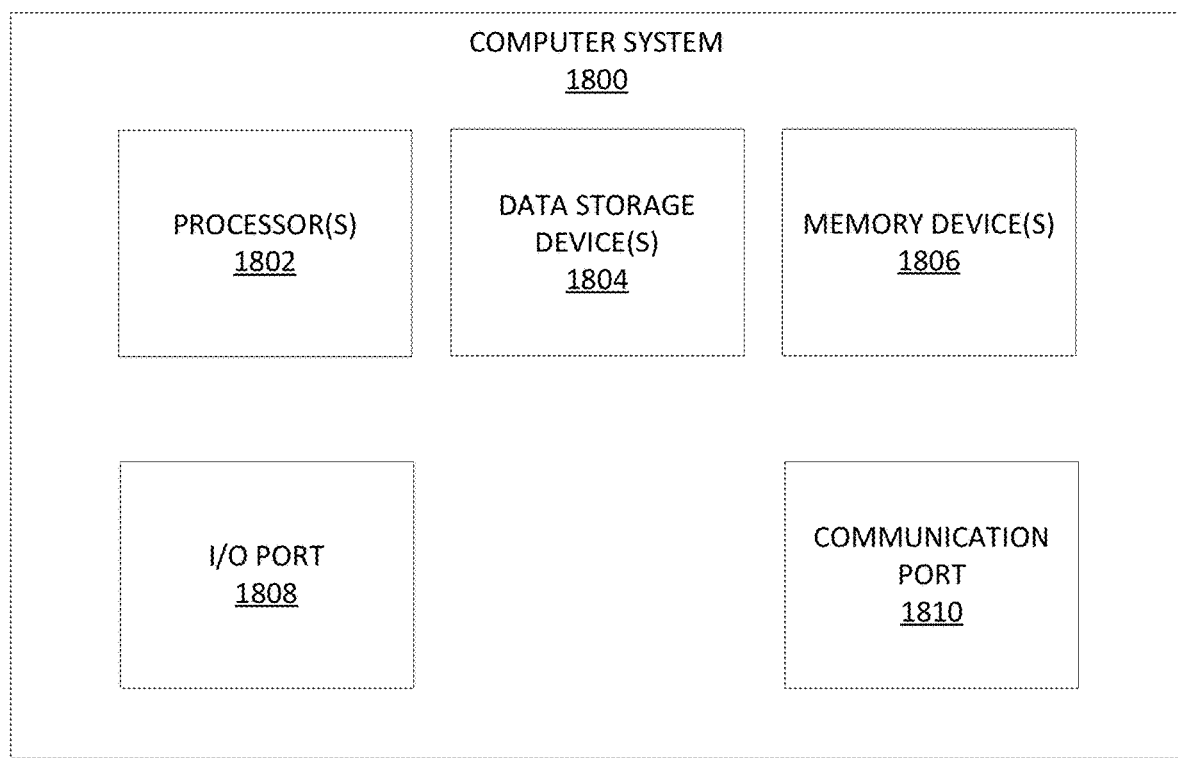
FIG. 18 is an example computing system having one or more computing units that may implement various systems and methods discussed herein.

Referring to FIG. 18, a detailed description of an example computing system 1800 having one or more computing units that may implement various systems and methods discussed herein is provided. The computing system 1800 may be applicable to any of the computers or systems utilized in the planning of the TAR procedure, and other computing or network devices. It will be appreciated that specific implementations of these devices may be of differing possible specific computing architectures not all of which are specifically discussed herein but will be understood by those of ordinary skill in the art.

The computer system 1800 may be a computing system that is capable of executing a computer program product to execute a computer process. Data and program files may be input to the computer system 1800, which reads the files and executes the programs therein. Some of the elements of the computer system 1800 are shown in FIG. 18, including one or more hardware processors 1802, one or more data storage devices 1804, one or more memory devices 1808, and/or one or more ports 1808-1810. Additionally, other elements that will be recognized by those skilled in the art may be included in the computing system 1800 but are not explicitly depicted in FIG. 18 or discussed further herein. Various elements of the computer system 1800 may communicate with one another by way of one or more communication buses, point-to-point communication paths, or other communication means not explicitly depicted in FIG. 18.

The processor 1802 may include, for example, a central processing unit (CPU), a microprocessor, a microcontroller, a digital signal processor (DSP), and/or one or more internal levels of cache. There may be one or more processors 1802, such that the processor 1802 comprises a single central-processing unit, or a plurality of processing units capable of executing instructions and performing operations in parallel with each other, commonly referred to as a parallel processing environment.

The computer system 1800 may be a conventional computer, a distributed computer, or any other type of computer, such as one or more external computers made available via a cloud computing architecture. The presently described technology is optionally implemented in software stored on the data stored device(s) 1804, stored on the memory device(s) 1806, and/or communicated via one or more of the ports 1808-1810, thereby transforming the computer system 1800 in FIG. 18 to a special purpose machine for implementing the operations described herein. Examples of the computer system 1800 include personal computers, terminals, workstations, mobile phones, tablets, laptops, personal computers, multimedia consoles, gaming consoles, set top boxes, and the like.

The one or more data storage devices 1804 may include any non-volatile data storage device capable of storing data generated or employed within the computing system 1800, such as computer executable instructions for performing a computer process, which may include instructions of both application programs and an operating system (OS) that manages the various components of the computing system 1800. The data storage devices 1804 may include, without limitation, magnetic disk drives, optical disk drives, solid state drives (SSDs), flash drives, and the like. The data storage devices 1804 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 1806 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 1804 and/or the memory devices 1806, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 1800 includes one or more ports, such as an input/output (I/O) port 1808 and a communication port 1810, for communicating with other computing, network, or other devices. It will be appreciated that the ports 1808-1810 may be combined or separate and that more or fewer ports may be included in the computer system 1800.

The I/O port 1808 may be connected to an I/O device, or other device, by which information is input to or output from the computing system 1800. Such I/O devices may include, without limitation, one or more input devices, output devices, and/or environment transducer devices.

In one implementation, the input devices convert a human-generated signal, such as, human voice, physical movement, physical touch or pressure, and/or the like, into electrical signals as input data into the computing system 1800 via the I/O port 1808. Similarly, the output devices may convert electrical signals received from computing system 1800 via the I/O port 1808 into signals that may be sensed as output by a human, such as sound, light, and/or touch. The input device may be an alphanumeric input device, including alphanumeric and other keys for communicating information and/or command selections to the processor 1802 via the I/O port 1808. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

In one implementation, a communication port 1810 is connected to a network by way of which the computer system 1800 may receive network data useful in executing the methods and systems set out herein as well as transmitting information and network configuration changes determined thereby. Stated differently, the communication port 1810 connects the computer system 1800 to one or more communication interface devices configured to transmit and/or receive information between the computing system 1800 and other devices by way of one or more wired or wireless communication networks or connections. Examples of such networks or connections include, without limitation, Universal Serial Bus (USB), Ethernet, Wi-Fi, Bluetooth®, Near Field Communication (NFC), Long-Term Evolution (LTE), and so on. One or more such communication interface devices may be utilized via the communication port 1810 to communicate one or more other machines, either directly over a point-to-point communication path, over a wide area network (WAN) (e.g., the Internet), over a local area network (LAN), over a cellular (e.g., third generation (3G) or fourth generation (4G)) network, or over another communication means. Further, the communication port 1810 may communicate with an antenna or other link for electromagnetic signal transmission and/or reception.

In an example implementation, patient data, bone models, transformation, mapping and shape matching software, tracking and navigation software, registration software, and other software and other modules and services may be embodied by instructions stored on the data storage devices 1804 and/or the memory devices 1806 and executed by the processor 1802. The computer system 1800 may be integrated with or otherwise form part of a surgical system for planning and performing a TAR procedure.

The system set forth in FIG. 18 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed herein may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure including any of the methods described herein may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium, optical storage medium; magneto-optical storage medium, read only memory (ROM); random access memory (RAM); erasable programmable memory (e.g., EPROM and EEPROM); flash memory; or other types of medium suitable for storing electronic instructions.

An example system for processing patient data so as to map weight bearing considerations from standing X-ray images to bones of a 3D bone model may include the following components: a network interface configured to receive one or more sets of patient data; a processing device in communication with the network interface; and a computer-readable medium in communication with the processing device configured to store information and instructions that, when executed by the processing device, performs the operations of: receiving first patient data 124, 126 comprising at least one two-dimensional (2D) image 124, 126 of a patient leg and foot 112 in a weighted pose. Additional operations may include receiving second patient data 114, 116 comprising computed tomography (CT) images 114, 116 of the patient leg and foot 112 in a non-weighted pose, where the first patient data 124, 126 and the second patient data 114, 116 are the result of separate imaging events. Additional operations may include generating a three-dimensional (3D) bone model 138 of the patient leg and foot 112 from the CT images 114, 116, where the 3D bone model 138 may include a plurality of 3D bone models representing individual bones of the patient leg and foot 112. Additional operations may include rearranging the plurality of 3D bone models 138 to mimic the weighted pose of the patient leg and foot 112 in the at least one 2D image 124, 126.

In certain instances, additional operations may include: generating a plurality of 2D projections of poses 212 of the plurality of 3D bone models 138; comparing the plurality of 2D projections 212 to contour lines 206, 208 outlining perimeters of bones of the patient leg and foot 112 in the at least one 2D image 124, 128; and identifying particular 2D projections 212g from the plurality of 2D projections 212 that best-fit a shape and size of the contour lines 206, 208.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

In general, while the embodiments described herein have been described with reference to particular embodiments, modifications can be made thereto without departing from the spirit and scope of the disclosure. Note also that the term "including" as used herein is intended to be inclusive, i.e. "including but not limited to."

What is claimed is:

1. A system for processing patient data associated with a joint of a patient, the joint formed by a first bone and a second bone, the system comprising:
   a computing device comprising a processing device and a computer-readable medium with one or more executable instructions stored thereon, wherein the processing device of the computing device executes the one or more executable instructions to perform the operations of:

generating a three-dimensional (3D) patient bone model of the joint that is representative of the joint of the patient in a non-weighted pose, the 3D patient bone model comprising a 3D first bone model of the first bone of the patient and a 3D second bone model of the second bone of the patient; and rearranging the 3D first bone model and the 3D second bone model relative to each other in order to mimic a weighted pose of the joint of the patient from at least one two-dimensional (2D) image of the joint of the patient in a weighted pose by:

generating a plurality of 2D projections of poses of the 3D patient bone model while excluding the generation of 2D projections of poses that violate permissible bio-kinematical relationships of bones making up the 3D patient bone model;

comparing the plurality of 2D projections to contour lines outlining perimeters of bones of the first bone and the second bone in the at least one 2D image;

identifying particular 2D projections from the plurality of 2D projections that best-fit a shape and size of the contour lines; and arranging the 3D first bone model and the 3D second bone model relative to each other according to orientations represented by the particular 2D projections that were identified, and arranging the 3D first bone model and the 3D second bone model relative to each other according to bone spacing in the weighted pose.

2. The system of claim 1, wherein the operations further include:

identifying landmarks in the 3D patient bone model;

building coordinate frames for the 3D first bone model and the 3D second bone model from the identified landmarks;

identifying permissible rotational and translational orientations between the coordinate frames of the 3D first bone model and the 3D second bone model; and providing a plurality of orientations for the 3D first bone model and the 3D second bone model within permissible rotational and translational orientations for the generation of the plurality of 2D projections of poses of the 3D first bone model and the 3D second bone model.

3. The system of claim 1, wherein the at least one 2D image comprises at least one X-ray image.

4. The system of claim 1, wherein the operations further include: planning a total knee replacement procedure or a total hip replacement procedure.

5. The system of claim 1, wherein the operations further include:

receiving a 3D image of the joint of the patient in the non-weighted pose, the 3D patient bone model of the joint that is representative of the joint of the patient in a non-weighted pose generated from the 3D image of the joint of the patient in the non-weighted pose.

6. The system of claim 5, wherein the 3D image of the joint of the patient in the non-weighted pose comprises at least one computed tomography image.

7. The system of claim 5, wherein the 3D image of the joint of the patient in the non-weighted pose comprises at least one magnetic resonance image.

8. The system of claim 1, wherein the operations further include: receiving the at least one 2D image of the joint of the patient in the weighted pose.

9. The system of claim 1, wherein the non-weighted pose is a non-standing pose.

10. The system of claim 1, wherein the weighted pose is a standing pose.

11. The system of claim 1, wherein the joint is a knee, the first bone is a femur, and the second bone is a tibia.

12. The system of claim 1, wherein the joint is a hip, the first bone is a femur, and the second bone is an ilium.

13. The system of claim 1, wherein the step of rearranging the 3D first bone model and the 3D second bone model relative to each other in order to mimic a weighted pose of the joint of the patient is at least partially automated.

14. A system for processing patient data associated with a joint of a patient, the joint formed by a first bone and a second bone, the system comprising:

a computing device comprising a processing device and a computer-readable medium with one or more executable instructions stored thereon, wherein the processing device of the computing device executes the one or more executable instructions to perform the operations of:

generating a three-dimensional (3D) patient bone model of the joint that is representative of the first bone and the second bone in a non-weighted pose, the 3D patient bone model comprising a 3D first bone model and a 3D second bone model representing the first bone and the second bone, respectively;

establishing coordinate frames for the 3D first bone model and the 3D second bone model from identified landmarks in the 3D patient bone model;

identifying permissible rotational and translational orientations between the coordinate frames of the 3D first bone model and the 3D second bone model based on bio-kinematics of bones represented by the 3D first bone model and the 3D second bone model; and rearranging the 3D first bone model and the 3D second bone model relative to each other to mimic a weighted pose of the joint of the patient as provided by at least one two-dimensional (2D) image of the joint of the patient in a weighted pose.

15. The system of claim 14, wherein rearranging the 3D first bone model and the 3D second bone model to mimic the weighted pose of the joint of the patient from the at least one 2D image of the joint of the patient in the weighted pose includes:

generating a plurality of 2D projections of poses of the 3D first bone model and the 3D second bone model while excluding the generation of 2D projections of poses that violate permissible bio-kinematical relationships of bones making up the 3D first bone model and the 3D second bone model;

comparing the plurality of 2D projections to contour lines outlining perimeters of bones of the first bone and the second bone in the at least one 2D image;

identifying particular 2D projections from the plurality of 2D projections that best-fit a shape and size of the contour lines; and arranging the 3D first bone model and the 3D second bone model according to orientations represented by the particular 2D projections that were identified, and arranging the 3D first bone model and the 3D second bone model relative to each other according to bone spacing in the weighted pose.

16. The system of claim 15, wherein the operations further include:

providing a plurality of orientations for the 3D first bone model and the 3D second bone model within permissible rotational and translational orientations for the generation of the plurality of 2D projections of poses of the 3D first bone model and the 3D second bone model.

17. The system of claim 14, wherein the at least one 2D image comprises at least one X-ray image.

18. The system of claim 14, wherein the operations further include: planning a total knee replacement procedure or a total hip replacement procedure.

19. The system of claim 14, wherein the operations further include: receiving a 3D image of the joint of the patient in the non-weighted pose, the 3D patient bone model of the joint of the patient in the non-weighted pose generated from the 3D image of the joint of the patient in the non-weighted pose.

20. The system of claim 19, wherein the 3D image of the joint of the patient in the non-weighted pose comprises at least one computed tomography image.

21. The system of claim 19, wherein the 3D image of the joint of the patient in the non-weighted pose comprises at least one magnetic resonance image.

22. The system of claim 14, wherein the operations further include: receiving the at least one 2D image of the joint of the patient in the weighted pose.

23. The system of claim 14, wherein the weighted pose is a standing pose.

24. The system of claim 14, wherein the joint is a knee, the first bone is a femur, and the second bone is a tibia.

25. The system of claim 14, wherein the joint is a hip, the first bone is a femur, and the second bone is an ilium.

26. The system of claim 14, wherein the step of rearranging the 3D first bone model and the 3D second bone model relative to each other to mimic a weighted pose of the joint of the patient is at least partially automated.

* * * * *